(12) United States Patent
Junghans et al.

(10) Patent No.: US 7,915,035 B2
(45) Date of Patent: Mar. 29, 2011

(54) VACCINE AGAINST ONCOVIRUS INFECTIONS SUCH AS INFECTIONS BY FELINE LEUKOSIS VIRUS OF THE CAT

(75) Inventors: Claas Junghans, Berlin (DE); Matthias Schroff, Berlin (DE); Christiane Juhls, Berlin (DE); Detlef Oswald, Berlin (DE); Hans Lutz, Rüdlingen (CH)

(73) Assignee: Mologen AG, Berlin (DE)

( * ) Notice: Subject to any disclaimer, the term of this patent is extended or adjusted under 35 U.S.C. 154(b) by 629 days.

(21) Appl. No.: 10/528,748

(22) PCT Filed: Sep. 23, 2003

(86) PCT No.: PCT/DE03/03179
§ 371 (c)(1),
(2), (4) Date: Mar. 13, 2006

(87) PCT Pub. No.: WO2004/028562
PCT Pub. Date: Apr. 8, 2004

(65) Prior Publication Data
US 2006/0240034 A1   Oct. 26, 2006

(30) Foreign Application Priority Data
Sep. 23, 2002   (DE) .................................. 102 44 863

(51) Int. Cl.
  C12N 15/00   (2006.01)
  C12N 1/20    (2006.01)
  C12N 15/86   (2006.01)
  C07H 21/02   (2006.01)
(52) U.S. Cl. .................. 435/320.1; 435/252.3; 435/455; 435/456; 536/23.1; 536/23.72
(58) Field of Classification Search ............... 435/320.1, 435/252.3, 455, 456; 536/23.1, 23.72
  See application file for complete search history.

(56) References Cited

U.S. PATENT DOCUMENTS
6,248,582 B1     6/2001   Khan et al.
6,348,196 B1     2/2002   Audonnet et al.
6,696,291 B2 *   2/2004   Shiver et al. ............... 435/339.1

FOREIGN PATENT DOCUMENTS
EP   0216564           4/1987
WO   WO 92/15672    *  9/1992
WO   WO 98/21322       5/1998
WO   WO 00/15824       3/2000
WO   WO 03/031470 A2   4/2003

OTHER PUBLICATIONS

Flynn Jn, et al., Feline leukaemia virus: protective immunity is mediated by virus-specific cytotoxic T lymphocytes.Immunology. Sep. 2000;101(1):120-5.*
www.kazusa.or.jp/codon/cgi-bin/showcodon.cgi?species=11824.*
Kennell, Principles and practices of nucleic acid hybridization. Progr. Nucleic Acid Res. Mol. Biol. 11: 259-301, 1971.*
Schirmbeck et al., Priming of immune responses to hepatitis B surface antigen with minimal DNA expression constructs modified with a nuclear localization signal peptide. J Mol Med. Jun. 2001;79(5-6):343-50.*
Laprevotte et al., Nucleotide sequence of the gag gene and gag-pol junction of feline leukemia virusJ. Virol. 50 (3), 884-894 (1984) and Genbank Accession No., K01803, FeLV gag cDNA.*
www.kazusa.or.jp/codon/cgi-bin/showcodon.cgi?species=11824 . 2002.*
"Protection of Cats Against Feline Leukemia Virus by Vaccination With a Canarypdx Virus Recombinant, ALVAC-FL," Tartaglia et al., Journal of Virology, Apr. 1993, p. 2370-2375, vol. 67, No. 4.
"Development of a Genetically Engineered Vaccine Against Feline Leukemia Virus Infection," Kensil et al., Javma, vol. 199, No. 10, Nov. 15,1991, p. 1423-1427.
"New Hope for an Aids Vaccine," H.L. Robinson, Nature Reviews, Immunology, vol. 2, Apr. 2002, p. 239-250.
"Increased Expression and Immunogenicity of Sequence-Modified Human Immunodeficiency Virus Type 1 Gag Gene," Megede et al., Journal of Virology, Mar. 2000, p. 2628-2635, vol. 74, No. 6.
"Human Immunodeficiency Virus Type 1-Specific Immunity After Genetic Immunization Is Enhanced by Modification of Gag and Pol Expression," Huang et al., Journal of Virology, May 2001, p. 4947-4951, vol. 75, No. 10.
"Feline Leukaemia Virus: Protective Immunity Is Mediated by Virus-Specific Cytotoxic T Lymphocytes," Flynn et al., Immunology 2000, 101, p. 120-125.

* cited by examiner

*Primary Examiner* — Maria Leavitt
(74) *Attorney, Agent, or Firm* — Ursula B. Day; Henry M. Feiereisen

(57) ABSTRACT

The invention concerns a vaccine that can induce protection against disease especially in consequence of a lentivirus infection, especially an infection with the Feline Leukosis virus. Such vaccine comprises codon-optimized DNA sequences encoding structural proteins and the most important membrane protein of FeLV.

20 Claims, 11 Drawing Sheets

Page 1 of Fig. 4

Figure 1:
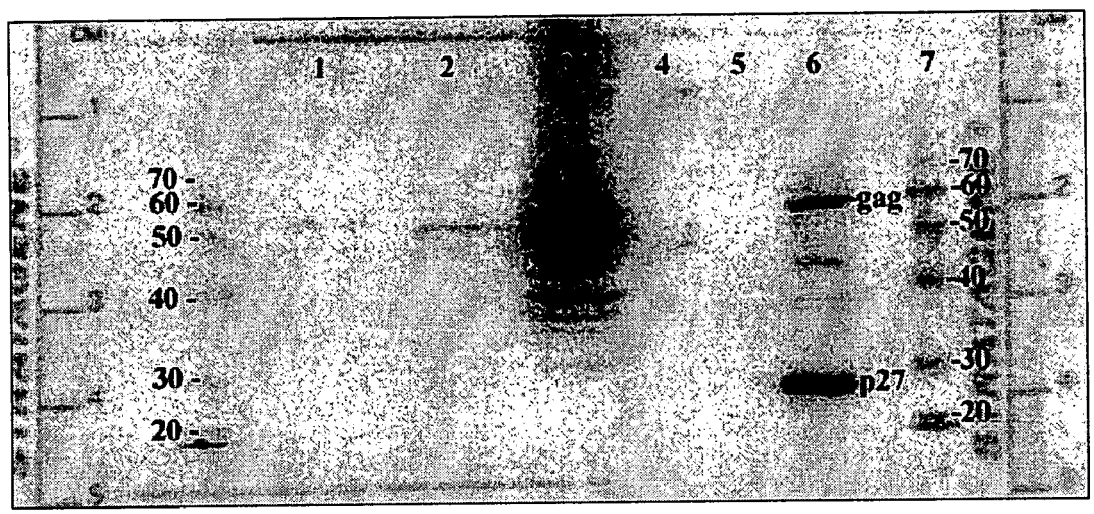
Figure 2:
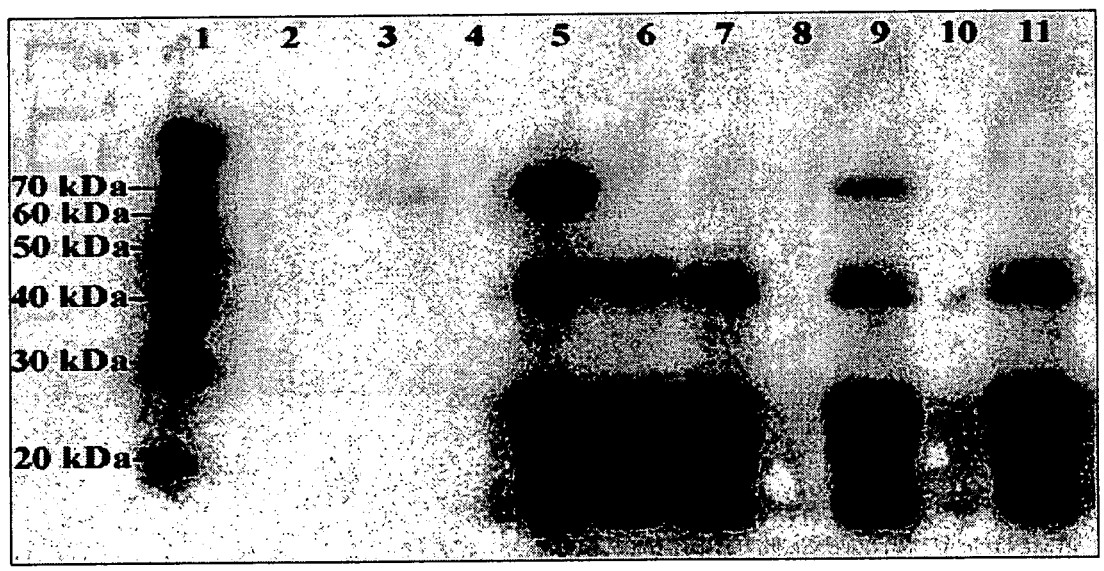

Fig. 4:   DNA sequence comparison of the wild type "gag" gene (Seq.ID2) against the codon-optimized "gag" gene (Seq.ID5).

```
SeqID2    1    ATGGGCCAAACTATAACTACCCCCTTGAGCCTCACCCTCAACCACTGGTCTGAGGTTCAG
SeqID5    1    """"""""""G""C""C""C""""""C""""""""G""""""G""""""""""AGC""""""G""""

SeqID2   61    GCACGGGCCCGTAATCAGGGTGTCGAAGTCCGGAAAAAGAAATGGATTACACTGTGTGAA
SeqID5   61    """CA""""""""A""G""""C""""""C""G""G""GA""""""G""""""G""""""C""""C""""""""C""""G

SeqID2  121    GCCGAATGGGTAATGATGAATGTAGGTTGGCCCCGAGAAGGAACTTTCACCATTGACAAT
SeqID5  121    """"""""G""""""""G""""""""""""""C""""G""C""""""""A""G""""G""""C""""C""""""""""""""""C""""""""""C

SeqID2  181    ATTTCACAGGTCGAGGAGAGAATCTTCGCCCCGGGGCCATATGGACACCCAGATCAAATC
SeqID5  181    """"CAGC""""""""""G""""""""""""""G""""""""""""""""""C""""C""""C""""C""""C""""""""C""""C""""G""""

SeqID2  241    CCTTATATTACCACGTGGAGATCCCTAGCCACAGACCCCCCTCCATGGGTTCGCCCATTC
SeqID5  241    """"C""""C""""C""""""""""""C""""""""GAG""""""G""""""""""C""""""""""""""""C""""C""""""""""GA""G""""C""""""""

SeqID2  301    CTACCCCCTCCTAAGCATCCCAGGACAGATCCTCCCGAGCCTCTTTCGCCGCAACCTCTT
SeqID5  301    """"G""""""""""C""""C""""""""""C""""""""""""""""""""C""""""C""""C""""""""""""""""""C""""GAGC""""C""""G""""C""""G

SeqID2  361    GCGCCGCAACCC_TC_TTCCCCCCA_CCCCGTCCTCTACCCCGTTCTCCCCAAACCAGAC
SeqID5  361    """"C""""C""""G""""""AG""GCC""""""""""""""T""AG""AG""""G""""""""""""""G""""G""""""""""G""""C""""""

SeqID2  418    CCCCCCAAGGCGCCTGTATTACCACCCAATCCTTCTTCCCCTTTAATTGATCTCTTAACA
SeqID5  421    """"""""""""""""""""""""""""""""""""""""""C""""C""""GC""G""""C""""""""""C""""CAGCAG""""""""CC""G""""C""""C""""GC""G""""C

SeqID2  478    GAAGAGCCACCTCCCTATCCTGGGGGTCACGGGCCAACACCGCCGTCAGGCCCTAGAACC
SeqID5  481    """"G""""""""""""C""""C""""""""""""""C""""C""""C""""C""""""""""""C""""C""""C""""C""""CAGC""""""""""""C""""G""""""""

SeqID2  538    CCAACTGCCTCCCCGATTGCCATCCGGCTGCGAGAACGACGAGAAAATCCAGCTGAGAAA
SeqID5  541    """"C""""C""""""AG""""""C""""C""""""""G""A""""""""""A""G""""GA""GA""G""""G""""C""""C""""C""""""""""G

SeqID2  598    TCTCAAGCCCTCCCCTTAAGGGAAGACCCAAACAACAGACCCCAGTACTGGCCATTCTCG
SeqID5  601    AGC""""G""""""""""""G""""""C""G""""""""""G""""""""""C""""""""""""""""""G""""""""""""""""""""""""""""""""""""""""""C""""""AGC

SeqID2  658    GCCTCTGACCTGTACAATTGGAAATTGCATAA_CCCCCCTTTCTCCCAGGACCCAGTGGC
SeqID5  661    """"""""AGC""""""""""""""""""""""""""""""""""""C""""""""""GC""""""""C""""C""""""""""""""""" _"AG""""""""""""""""""""C""""""""""

SeqID2  717    CCTAACTAACCTAATTGAGTCCATTTTAGTGACACATCAGCCAACCTGGGACGACTGCCA
SeqID5  720    """"""""G""""C""""""""""""""G""""C""""""AG""""""CC""G""""""""""C""""C""""""""""C""""""""""""""""""""""""""""""""""""""""""""

SeqID2  777    ACAGCTCTTACAGGCTCTCCTGACGGCAGAGGAGAGACAAAGGGTCCTCCTTGAAGCCCG
SeqID5  780    G""""""""""""GC""G""""""""""""C""""G""""""""""""C""""C""""""""""""""""G""""G""""""""""G""""G""""G""""G""""""A""

SeqID2  837    AAAGCAAGTTCCAGGCGAGGACGGACGGCCAACCCAGCTGCCCAATGTCGTTGACGAGGC
SeqID5  840    G""""""""""G""""G""""C""""""""""""""""""""""""""CA""""""""C""""""""""""""""""""""""""""""C""""G""""G""""""""""""""

SeqID2  897    TTTCCCCTTGACCCGTCCCAACTGGGATTTTTGTACGCCGGCAGGTAGGGAGCACCTACG
SeqID5  900    C""""""""""""C""""""""""A""G""""""""""""""""""""""""C""""C""""C""""C""""C""""""C""""C""""""""""""""""""""""""""GA""

SeqID2  957    CCTTTATCGCCAGTTGCTGTTAGCGGGGCTCCGCGGGGCTGCAAGACGCCCCACTAATTT
SeqID5  960    G""""G""""CA""G""""""C""""""""""C""G""""C""""C""""GA""G""""C""""C""""""C""""GA""G""""""""""C""""CC""

SeqID2 1017    GGCACAGGTAAAGCAAGTTGTACAAGGGAAAGAGGAAACGCCAGCCTCATTCTTAGAAAG
SeqID5 1020    """""""C""""""""""G""""""""G""""G""""G""""G""""C""""G""""""""""G""""A""""C""""""""AGC""""""""C""""G""""G""""

SeqID2 1077    ATTAAAAGAGGCTTACAGAATGTATACTCCCTATGACCCTGAGGACCCAGGGCAGGCTGC
SeqID5 1080    GC""G""""G""""""""""""""""C""""""""""G""""""""""""C""""C""""""""""C""""""""""C""""""""""""""""""""""C""""C""""""""""""CA""

SeqID2 1137    TAGTGTTATCCTGTCCTTTATCTACCAGTCTAGCCCGGACATAAGAAATAAGTTACAAAG
SeqID5 1140    C""""C""""G""""""""""""""AG""""""C""""""""""""""""""""AGC""""""""""C""""""""""""C""""G""""C""""""C""""G""""G""""""
```

Page 2 of Fig. 4

```
SeqID2   1197   GCTAGAAGGCCTACAGGGGTTCACACTGTCTGATTTGCTAAAAGAGGCAGAAAAGATATA
SeqID5   1200   """G""G"""""G"""""C"""""C"""AGC""CC"""G""G"""""C""G"""""C""

SeqID2   1257   CAACAAAAGGGAAACCCCAGAGGAAAGGGAAGAAAGATTATGGCAGCGGCAGGAAGAAAG
SeqID5   1260   """""G"""""G""A""C""""G""""G""G""GC"G"""""A""""""G""G""

SeqID2   1317   AGATAAAAAGCGCCATAAGGAGATGACTAAAGTTCTGGCCACAGTAGTTGCTCAGAATAG
SeqID5   1320   G""C""G"""A""G""C"""""""""""C""G""G"""""""C""G""G""C"""""C""

SeqID2   1377   AGATAAGGATAGAGGGGAAAGTAAACTGGGAGATCAAAGGAAAATACCTCTGGGGAAAGA
SeqID5   1380   G""C""""""C""G""C""G""C""G""""C""C""G"""""G""C""C"""""C""G""

SeqID2   1437   CCAGTGTGCCTATTGCAAGGAAAAGGGACATTGGGTTCGCGATTGCCCGAAACGACCCCG
SeqID5   1440   """""""C"""""C""""""""G"""""C""C"""""GA"G""C""""C""GA"G"""A"

SeqID2   1497   GAAGAAACCCGCCAACTCCACTCTCCTCTAA
SeqID5   1500   """""G""""""""""AG"""C""G""G""G
```

Page 1 of Fig. 5

Fig. 5  DNA sequence comparison of the wild type „env" (gp70 region from Seq.ID1) against the codon- and signal optimized „env" gene (gp70; Seq.ID8).

```
SeqID11     1 ATGGAAAGTCCAACGCACCCAAAACCCTCTAAAGATAAGACTCTCTCGTGGAACTTAGCG
SeqID8      1 """""GTCC"""C""C"""""C""G"""""C""G""C"""""C""G""C"""""A"G"T"

SeqID11    61 TTTCTGGTGGGGATCTTATTTACAATAGACATAGGAATGGCCAATCCTAGTCCACACCAA
SeqID8     61 """C"""""""""C"""C"G""C""C""T"""""T""C"""""""""C""CTCC"""C""C""GG

SeqID11   121 ATATATAATGTAACTTGGGTAATAACCAATGTACAAACTAACACCCAAGCTAACGCCACC
SeqID8    121 """C"""C""""""G""C"""""G""C"""""""""G""G""C"""""""""G""C""T"""""

SeqID11   181 TCTATGTTAGGAACCTTAACCGATGCCTACCCTACCCTACATGTTGACTTATGTGACCTA
SeqID8    181 """"""""C"G""C"""C"G""A"""""A"""""C"""""G"""""G"""C"G"""""""""G

SeqID11   241 GTGGAGACACCTGGGAACCTATAGTCCTAAACCCAACCAATGTAAAACACGGGGCACGT
SeqID8    241 """""G"""""""""""G""C""TCCG""G"""""C"""""""""G""G""T"""""CA"G

SeqID11   301 TACTCCTCCTCAAAATATGGATGTAAAACTACAGATAGAAAAAAACAGCAACAGACATAC
SeqID8    301 """""""""""""C""G"""""C""C""G""C"""""C""G""G""G"""""G"""""C"""

SeqID11   361 CCCTTTTACGTCTGCCCCGGACATGCCCCCTCGTTGGGGCCAAAGGGAACACATTGTGGA
SeqID8    361 """""C"""T""G"""""T""C""""""""""""CC"""""C""C"""""C""C""C"""""G

SeqID11   421 GGGGCACAAGATGGGTTTTGTGCCGCATGGGGATGTGAGACCACCGGAGAAGCTTGGTGG
SeqID8    421 """""C""G"""""C""C"""""T""C"""""C"""""A"""""A""G""G""C"""""

SeqID11   481 AAGCCCACCTCCTCATGGGACTATATCACAGTAAAAAGAGGGAGTAGTCAGGACAATAGC
SeqID8    481 """"""""""""""C"""""""C"""""""G""G""G""CTCCTCC"""""""CTC"

SeqID11   541 TGTGAGGGAAAATGCAACCCCCTGGTTTTGCAGTTCACCCAGAAGGGAAGACAAGCCTCT
SeqID8    541 """""""""C""G"""""""""""""""GC"""""""""""""""""""C""G""G"""""C

SeqID11   601 TGGGACGGACCTAAGATGTGGGGATTGCGACTATACCGTACAGGATATGACCCTATCGCT
SeqID8    601 """""""T""C""C"""""""""""CC""A"G""G""A"G"""""C"""""""C""T""C

SeqID11   661 TTATTCACGGTGTCCCGGCAGGTATCAACCATTACGCCGCCTCAGGCAATGGGACCAAAC
SeqID8    661 C"G"""""A"""""""A"""""""""G""C"""""C""C""C"""""""C"""""C""C"""

SeqID11   721 CTAGTCTTACCTGATCAAAAACCCCCATCCCGACAATCTCAAACAGGGTCCAAAGTGGCG
SeqID8    721 """G""GC"G"""""C""G""G"""""C"""A"G""G""C""G"""""C"""""G"""""C

SeqID11   781 ACCCAGAGGCCCCAAACGAATGAAAGCGCCCCAAGGTCTGTTGCCCCCACCACCATGGGT
SeqID8    781 """"""""""""""""G""C"""""GTCT"""""C""""""""G""""""""""""""""C

SeqID11   841 CCCAAACGGATTGGGACCGGAGATAGGTTAATAAATTTAGTACAAGGGACATACCTAGCC
SeqID8    841 """""GA"""""""""C""A""G""C"""C"G""C"""CC"G""G""G""C""C"""""G"""

SeqID11   901 TTAAATGCCACCGACCCCAACAAAACTAAAGACTGTTGGCTCTGCCTGGTTTCTCGACCA
SeqID8    901 C"G"""""""""A"""""""""""""G""C""G"""""C"""""G"""""""""G""CA"G""C

SeqID11   961 CCCTATTACGAAGGGATTGCAATCTTAGGTAACTACAGCAACCAAACAAACCCCCCCCCA
SeqID8    961 """""C""T""G""C"""""C"""C""G""C"""""TC"""""G""C"""""""""""""C

SeqID11  1021 TCCTGCCTATCTACTCCGCAACACAAACTAACTATATCTGAAGTATCAGGGCAAGGAATG
SeqID8   1021 """""""""G""C""C""C""G"""""G""G""C""C"""""G""G""T""C""G""C"""

SeqID11  1081 TGCATAGGGACTGTTCCTAAAACCCACCAGGCTTTGTGCAATAAGACACAACAGGGACAT
SeqID8   1081 """""T""C""A""G""C""G"""""""""CC"""""""C"""""C""G"""""C""C

SeqID11  1141 ACAGGGGCGCACTATCTAGCCGCCCCCAACGGCACCTATTGGGCCTGTAACACTGGACTC
SeqID8   1141 """""""""""C"""""""C""G""T""T"""""T"""""""""C"""""C"""""A""C""G
```

Page 2 of Fig. 5

```
SeqID11  1201 ACCCCATGCATTTCCATGGCGGTGCTCAATTGGACCTCTGATTTTTGTGTCTTAATCGAA
SeqID8   1201 """""C"""""C""""""""T"""""G""C""""""""""""C""C"""""GC"G""T""G

SeqID11  1261 TTATGGCCCAGAGTGACTTACCATCAACCCGAATATGTGTACACACATTTTGCCAAAGCT
SeqID8   1261 C"G"""""""""G""""C"""""C""G""T""G"""""""""""""C""C"""""""G"""

SeqID11  1321 GTCAGGTTCCGAAGAGAACCAATATCACTAACGGTTGCCCTTATGTTGGGAGGACTTACT
SeqID8   1321 """G"""""""A"G""G""G""C""C""C""G""A""G""""""G"""C"""""G""C""G""A

SeqID11  1381 GTAGGGGGCATAGCCGCGGGGGTCGGAACAGGGACTAAAGCCCTCCTTGAAACAGCCTGA
SeqID8   1381 """G"""""""""T""T""T"""""G""C"""""C""C""G"""""G""G"""""""""""
```

Page 1 of Fig. 6

Fig. 6 DNA sequence comparison of the wild type „env" gene (Seq.ID1) against the codon- and signal optimized „env" gene (gp85) (Seq.ID7).

```
SeqID1     1 ATGGAAAGTCCAACGCACCCAAAACCCTCTAAAGATAAGACTCTCTCGTGGAACTTAGCG
SeqID7     1 """""GTCC""C""C"""""C""G"""""C""G""C"""""C""G""C"""""A"G"T"

SeqID1    61 TTTCTGGTGGGGATCTTATTTACAATAGACATAGGAATGGCCAATCCTAGTCCACACCAA
SeqID7    61 ""C""""""""""C"""C"G""C""C""T"""""T""C"""""""""C""CTCC""C"C""GG

SeqID1   121 ATATATAATGTAACTTGGGTAATAACCAATGTACAAACTAACACCCAAGCTAACGCCACC
SeqID7   121 """C""C"""""G""C"""""G""C"""""""""G""G""C"""""""""G""C""T"""""

SeqID1   181 TCTATGTTAGGAACCTTAACCGATGCCTACCCTACCCTACATGTTGACTTATGTGACCTA
SeqID7   181 """"""C"G""C"""C"G""A"""""A"""""C"""""G"""""G"""C"G"""""""""G

SeqID1   241 GTGGGAGACACCTGGGAACCTATAGTCCTAAACCCAACCAATGTAAAACACGGGGCACGT
SeqID7   241 """""G""""""""""""G""C""TCCG""G"""""C"""""""""G""G""T"""""CA"G

SeqID1   301 TACTCCTCCTCAAAATATGGATGTAAAACTACAGATAGAAAAAAACAGCAACAGACATAC
SeqID7   301 """"""""""""C""G"""""C""C""G""C"""""C""G""G""G"""""G"""""C"""

SeqID1   361 CCCTTTTACGTCTGCCCCGGACATGCCCCCTCGTTGGGGCCAAAGGGAACACATTGTGGA
SeqID7   361 """""C""T""G"""""T""C"""""""""""CC"""""C""C"""""C""C""C"""""G

SeqID1   421 GGGGCACAAGATGGGTTTTGTGCCGCATGGGGATGTGAGACCACCGGAGAAGCTTGGTGG
SeqID7   421 """""C""G"""""C""C"""""T""C"""""C"""""A"""""A""G""G""C"""""""

SeqID1   481 AAGCCCACCTCCTCATGGGACTATATCACAGTAAAAAGAGGGAGTAGTCAGGACAATAGC
SeqID7   481 """""""""""""""""C""""""""""C"""""""""G""G""G""CTCCTCC"""""""CTC"

SeqID1   541 TGTGAGGGAAAATGCAACCCCCTGGTTTTGCAGTTCACCCAGAAGGGAAGACAAGCCTCT
SeqID7   541 """""""""C""G""""""""""""""""GC"""""""""""""""""""""""C""G""G"""""C

SeqID1   601 TGGGACGGACCTAAGATGTGGGGATTGCGACTATACCGTACAGGATATGACCCTATCGCT
SeqID7   601 """""""T""C""C""""""""""""""CC""A"G""G"""A"G"""""C"""""""""C""T""C

SeqID1   661 TTATTCACGGTGTCCCGGCAGGTATCAACCATTACGCCGCCTCAGGCAATGGGACCAAAC
SeqID7   661 C"G"""""A"""""A"""""""""G""C"""""C""C""C""C"""""C"""""C""C"""

SeqID1   721 CTAGTCTTACCTGATCAAAAACCCCCATCCCGACAATCTCAAACAGGGTCCAAAGTGGCG
SeqID7   721 ""G""GC"G"""""C""G""G"""""C""A"G""G""C""G"""""C"""""G"""""C

SeqID1   781 ACCCAGAGGCCCCAAACGAATGAAAGCGCCCCAAGGTCTGTTGCCCCCACCACCATGGGT
SeqID7   781 """""""""""""G""C"""""GTCT"""""C"""""""""G"""""""""""""""""C

SeqID1   841 CCCAAACGGATTGGGACCGGAGATAGGTTAATAAATTTAGTACAAGGGACATACCTAGCC
SeqID7   841 """""GA"""""""""C""A""G""C"""C"G""C""CC"G""G""G""C""C"""""G"""

SeqID1   901 TTAAATGCCACCGACCCCAACAAAACTAAAGACTGTTGGCTCTGCCTGGTTTCTCGACCA
SeqID7   901 C"G"""""""""A"""""""""""""G""C""G"""""C"""""G"""""""""G""CA"G""C

SeqID1   961 CCCTATTACGAAGGGATTGCAATCTTAGGTAACTACAGCAACCAAACAAACCCCCCCCCA
SeqID7   961 """""C""T""G""C"""""C"""C"G""C"""""""TC"""""G""C"" """""""C

SeqID1  1021 TCCTGCCTATCTACTCCGCAACACAAACTAACTATATCTGAAGTATCAGGGCAAGGAAT
SeqID7  1020 C"""""""""G""C""C""C""G"""""G""G""C""C"""""G""G""T"C""G""C""

SeqID1  1080 GTGCATAGGGACTGTTCCTAAAACCCACCAGGCTTTGTGCAATAAGACACAACAGGGACA
SeqID7  1080 """""T""C""A""G""C""G"""""""""CC"""""""""C"""""C""G"""""C""

SeqID1  1140 TACAGGGGCGCACTATCTAGCCGCCCCCAACGGCACCTATTGGGCCTGTAACACTGGACT
SeqID7  1140 C"""""""""C"""""C""G""T"T"""""T"""""""""C"""""""""C"""""A"C""
```

Page 2 of Fig. 6

```
SeqID1  1200  CACCCCATGCATTTCCATGGCGGTGCTCAATTGGACCTCTGATTTTTGTGTCTTAATCGA
SeqID7  1200  G"""""C"""""C""""""""T""""G""C"""""""""""C""C""""GC"G""T""

SeqID1  1260  ATTATGGCCCAGAGTGACTTACCATCAACCCGAATATGTGTACACACATTTTGCCAAAGC
SeqID7  1260  GC"G""""""""G"""""C""""C""G""T""G""""""""""C""C"""""""G""

SeqID1  1320  TGTCAGGTTCCGAAGAGAACCAATATCACTAACGGTTGCCCTTATGTTGGGAGGACTTAC
SeqID7  1320  """G""""""A"G""G""G""C""C""C""G""A"G""""G""C""""G""C""G""

SeqID1  1380  TGTAGGGGGCATAGCCGCGGGGGTCGGAACAGGGACTAAAGCCCTCCTTGAAACAGCCCA
SeqID7  1380  A""G""""""""T""T""T""""G""C""""C""C""G""""G""G""""""""""

SeqID1  1440  GTTCAGACAACTACAAATGGCCATGCACACAGACATCCAGGCCCTAGAAGAATCAATTAG
SeqID7  1440  """"""""""""""""""""""""""""""""""""""""""""""""G"""G""""

SeqID1  1500  TGCCTTAGAAAAGTCCCTGACCTCCCTTTCTGAAGTAGTCTTACAAAACAGACGGGGCCT
SeqID7  1500  C""T""""""A"""""""""""""""C""""""""""""C""""""""""""A"""""

SeqID1  1560  AGATATTCTATTCTTACAAGAGGGAGGGCTCTGTGCCGCATTGAAAGAAGAATGTTGCTT
SeqID7  1560  """""""""""C""""""""""""A"""""""""""A"""""""""""""""T""

SeqID1  1620  CTATGCGGATCACACCGGACTCGTCCGAGACAATATGGCCAAATTAAGAGAAAGACTAAA
SeqID7  1620  T""""A"""""""""""T"A"""""""T"""""""T"""""""""""""""T"""

SeqID1  1680  ACAGCGGCAACAACTGTTTGACTCCCAACAGGGATGGTTTGAAGGATGGTTCAACAAGTC
SeqID7  1680  """"""""""""""""""""""""""""""""""""""""""""""""""""""""""

SeqID1  1740  CCCCTGGTTTACAACCCTAATTTCCTCCATTATGGGCCCCTTACTAATCCTACTCCTAAT
SeqID7  1740  """""""C""""""""""""""""""""T"""""""""""""G""T""""G""""""

SeqID1  1800  TCTCCTCTTCGGCCCATGCATCCTTAACCGATTAGTACAATTCGTAAAAGACAGAATATC
SeqID7  1800  """"""""""""""""""""""""""""""""""G""G""""""""""""""""""""

SeqID1  1860  TGTGGTACAGGCTTTAATTTTAACCCAACAGTACCAACAGATAAAGCAATACGATCCGGA
SeqID7  1860  G"""""""A""C"""G"""""""""""""""""""""""""""""""""""""""""""

SeqID1  1920  CCGACCATGA
SeqID7  1920  """"""""""
```

Fig. 7    Protein sequence comparison of the wild type "gag" protein (Seq.ID4) against the protein sequence of the codon-optimized "gag" protein (Seq.ID6).

```
SeqID4    1   MGQTITTPLSLTLNHWSEVQARARNQGVEVRKKKWITLCEAEWVMMNVGWPREGTFTIDN
SeqID6...1    """"""""""""""""""""""""""""""""""""""""""""""""""""""""""

SeqID4...61   ISQVEERIFAPGPYGHPDQIPYITTWRSLATDPPPWVRPFLPPPKHPRTDPPEPLSPQPL
SeqID6...61   """"""""""""""""""""""""""""""""""""""""""""""""""""""""""""

SeqID4...121  APQPSSPHPV_LYPVLPKPDPPKAPVLPPNPSSPLIDLLTEEPPPYPGGHGPTPPSGPRT
SeqID6...121  """"""A"PISS""""""""""""""""""""""""""""""""""""""""""""""""

SeqID4...180  PTASPIAIRLRERRENPAEKSQALPLREDPNNRPQYWPFSASDLYNWKLHNPPFSQDPVA
SeqID6...181  """"""""S"""""""""""""""""""""""""""""""""""""""""""""""""""

SeqID4...240  LTNLIESILVTHQPTWDDCQQLLQALLTAEERQRVLLEARKQVPGEDGRPTQLPNVVDEA
SeqID6...241  """"""""""""""""""""""""""""""""""""""""""""""""""""""""""""

SeqID4...300  FPLTRPNWDFCTPAGREHLRLYRQLLLAGLRGAARRPTNLAQVKQVVQGKEETPASFLER
SeqID6...301  """"""""""""""""""""""""""""""""""""""""""""""""""""""""""""

SeqID4...360  LKEAYRMYTPYDPEDPGQAASVILSFIYQSSPDIRNKLQRLEGLQGFTLSDLLKEAEKIY
SeqID6...361  """"""""""""""""T"""""""""""""""""""""""""""""""""""""""""""

SeqID4...420  NKRETPEEREERLWQRQEERDKKRHKEMTKVLATVVAQNRDKDRGESKLGDQRKIPLGKD
SeqID6...421  """"""""""""""""""""""""""""""""""""""""""""""""""""""""""""

SeqID4...480  QCAYCKEKGHWVRDCPKRPRKKPANSTLL
SeqID6...481  """""""""""""""""""""""""""""
```

Fig. 8    Protein sequence comparison of the wild type „env" protein (Seq.ID3) against the protein sequence of the codon- and signal optimized „env" protein (gp70) (Seq.ID10).

```
SeqID3    1   MESPTHPKPSKDKTLSWNLAFLVGILFTIDIGMANPSPHQIYNVTWVITNVQTNTQANAT
SeqID10   1   """""""""""""""MV"""""""""""""""""""""PR"""""""""""""""""""

SeqID3   61   SMLGTLTDAYPTLHVDLCDLVGDTWEPIVLNPTNVKHGARYSSSKYGCKTTDRKKQQQTY
SeqID10  61   """"""""""""""""""""""""""""""P"""""""""""""""""""""""""""""

SeqID3  121   PFYVCPGHAPSLGPKGTHCGGAQDGFCAAWGCETTGEAWWKPTSSWDYITVKRGSSQDNS
SeqID10 121   """"""""""""""""""""""""""""""""""""""""""""""""""""""""""""

SeqID3  181   CEGKCNPLVLQFTQKGRQASWDGPKMWGLRLYRTGYDPIALFTVSRQVSTITPPQAMGPN
SeqID10 181   """"""""""""""""""""""""""""""""""""""""""""""""""""""""""""

SeqID3  241   LVLPDQKPPSRQSQTGSKVATQRPQTNESAPRSVAPTTMGPKRIGTGDRLINLVQGTYLA
SeqID10 241   """"""""""""""""""""""""""""""""""""""""""""""""""""""""""""

SeqID3  301   LNATDPNKTKDCWLCLVSRPPYYEGIAILGNYSNQTNPPPSCLSTPQHKLTISEVSGQGM
SeqID10 301   """"""""""""""""""""""""""""""""""""""""""""""""""""""""""""

SeqID3  361   CIGTVPKTHQALCNKTQQGHTGAHYLAAPNGTYWACNTGLTPCISMAVLNWTSDFCVLIE
SeqID10 361   """"""""""""""""""""""""""""V"""""""""""""""""""""""""""""""

SeqID3  421   LWPRVTYHQPEYVYTHFAKAVRFRREPISLTVALMLGGLTVGGIAAGVGTGTKALLETA
SeqID10 421   """"""""""""""""""""""""""""""""""""""""""""""""""""""""""
```

Fig. 9  Protein sequence comparison of the wild type „env" protein (Seq.ID3) against the protein sequence of the codon- and signal optimized „env" protein (gp85) (Seq.ID9).

```
SeqID3    1   MESPTHPKPSKDKTLSWNLAFLVGILFTIDIGMANPSPHQIYNVTWVITNVQTNTQANAT
SeqID9    1   """""""""""""""""MV""""""""""""""""""""""PR"""""""""""""""""

SeqID3   61   SMLGTLTDAYPTLHVDLCDLVGDTWEPIVLNPTNVKHGARYSSSKYGCKTTDRKKQQQTY
SeqID9   61   """""""""""""""""""""""""""""""""P""""""""""""""""""""""""""

SeqID3  121   PFYVCPGHAPSLGPKGTHCGGAQDGFCAAWGCETTGEAWWKPTSSWDYITVKRGSSQDNS
SeqID9  121   """"""""""""""""""""""""""""""""""""""""""""""""""""""""""""

SeqID3  181   CEGKCNPLVLQFTQKGRQASWDGPKMWGLRLYRTGYDPIALFTVSRQVSTITPPQAMGPN
SeqID9  181   """"""""""""""""""""""""""""""""""""""""""""""""""""""""""""

SeqID3  241   LVLPDQKPPSRQSQTGSKVATQRPQTNESAPRSVAPTTMGPKRIGTGDRLINLVQGTYLA
SeqID9  241   """"""""""""""""""""""""""""""""""""""""""""""""""""""""""""

SeqID3  301   LNATDPNKTKDCWLCLVSRPPYYEGIAILGNYSNQTNPPPSCLSTPQHKLTISEVSGQGM
SeqID9  301   """"""""""""""""""""""""""""""""""""""""""""""""""""""""""""

SeqID3  361   CIGTVPKTHQALCNKTQQGHTGAHYLAAPNGTYWACNTGLTPCISMAVLNWTSDFCVLIE
SeqID9  361   """"""""""""""""""""""""""""""V"""""""""""""""""""""""""""""

SeqID3  421   LWPRVTYHQPEYVYTHFAKAVRFRREPISLTVALMLGGLTVGGIAAGVGTGTKALLETAQ
SeqID9  421   """"""""""""""""""""""""""""""""""""""""""""""""""""""""""""

SeqID3  481   FRQLQMAMHTDIQALEESISALEKSLTSLSEVVLQNRRGLDILFLQEGGLCAALKEECCF
SeqID9  481   """"""""""""""V"""""""""""""""""""""""""""""""""""""""""""""

SeqID3  541   YADHTGLVRDNMAKLRERLKQRQQLFDSQQGWFEGWFNKSPWFTTLISSIMGPLLILLLI
SeqID9  541   """"""""""""""""""""""""""""""""""""""""""""""""""L"""""""""

SeqID3  601   LLFGPCILNRLVQFVKDRISVVQALILTQQYQQIKQYDPDRP
SeqID9  601   """"""""""""""""""""""""""""""V""""""""""
```

VACCINE AGAINST ONCOVIRUS INFECTIONS SUCH AS INFECTIONS BY FELINE LEUKOSIS VIRUS OF THE CAT

CROSS-REFERENCES TO RELATED APPLICATIONS

This application is the U.S. National Stage of International Application No. PCT/DE 2003, filed Sep. 9, 2003, which designated the United States and has been published as International Publication No. WO2004 028562 and which claims the priority of German Patent Application, Serial No. 10 244 863.9 filed Sep. 23, 2002, pursuant to 35 U.S.C. 119(a)-(d).

BACKGROUND OF THE INVENTION

The invention concerns a vaccine on the basis of DNA, by which cats can be protected against infections with Feline Leukosis virus.

Feline Leukosis virus (FeLV) is a cat-specific, world wide endemic virus that causes severe disease and is one of the main causes of mortality in feline populations. Currently, the infection rate is between 12% to 16% in cats both in Europe and the USA.

Some of the cats can surmount the infection; however a life long persistence of virus in the organism is also possible. Latently infected cats are then deemed to be a reservoir of pathogens.

An efficacious therapy of FeLV infections leading to eradication of the disease is currently not possible. The best success currently is to push back the disease for some time. Certain chemotherapeutic agents can be applied to cats; side effects however are highly problematic, as they are in human medicine. The treatment of interferons is experimental currently.

Virostatic drugs are not capable to inactivate and thus also do not lead to a success definable as healing.

An effective management of FeLV infections can only be effected preventively by vaccination.

STATE OF THE ART

Vaccines that are currently available either are based on inactivated FeLV viruses, on proteins produced by recombinant methods, so-called subunit vaccines, or on the use of genetically modified live vaccines. These classes of vaccines, however, show a number of disadvantages, apart from an unsatisfactory success of vaccination.

Preparations from inactivated viruses lead to the desired immunity only in a part of the vaccinated animals. These vaccines invariably consist of protein mixtures, in which highly immunogenic antigens have to compete with a lot of other proteins for the presentation by the immune system. Furthermore, after the vaccination strong side effects such as allergic reactions and autoimmune disease can occur.

A recombinant vaccine consisting of coat protein of FeLV produced by biotechnological methods, adjuvantated by aluminium hydroxide and saponin, is a vaccine frequently employed currently. Vaccination with this vaccine lead to protection against leukosis in 80% to 95% of the cats (Lutz et al., 1991, J Am Vet Med Assoc; 199(10): 1446-52).

A problem is the risk of the occurrence of fibrosarcoma at the site of vaccination. Another disadvantage of this vaccine is that the raised immunity is mainly based on the production of virus neutralising antibodies. Newer experimental results (Flynn et al., 2000, Immunology 101, 120-125) however show that for the formation of protective immunity, the cellular immune response is also of great importance.

The use of live vaccines has proven to be effective with regard to the effected immunity, however it contains the inherent risk that the virus strains employed convert to new pathogenic viral strains by mutation or recombination. Also there has to be observed that when using such vaccines that contain all viral structures, it cannot be discriminated after immunisation whether the animals were infected or vaccinated. For those two reasons, these vaccines are not suitable for practice.

Another example for a vaccine consisting of virus capable of infecting or replicating is a recombinant canary poxvirus expressing FeLV surface proteins. In experimental infections, 83% of the animals were protected from infection (Jarrett et al., 1993, J of Virology: 2370-2375). This vaccine however comprises the disadvantages of a live vaccine with regard to unpredictable recombinations; furthermore it is relatively difficult and hence, expensive to produce and to characterize.

Apart from such classic and modern recombinant vaccines, the possibility exists to vaccinate with DNA expression constructs. Only the information for certain immunogenic parts of the pathogen in the form of DNA is thereby given to the vaccinee. After vaccination, FeLV antigens are expressed by the cells of the vaccinated cat and stimulate an immune response against the virus in this way.

This possibility to attain an immune response against an antigen by injection of DNA expression constructs encoding this antigen was first published by Tang and Ulmer for the mouse (Tang et al., 1992, Nature 365, 152-154; Ulmer et al., 1993 Science 259, 1745-1749) and has been demonstrated in a great number of species since. It can be assumed that the general principle of vaccination with nucleic acids that encode immunogen is applicable to all higher animals. Regarding the selection of suitable antigens, their encoding into nucleic acid sequences and the selection of a suitable vaccination regime, however, any application poses a number of problems some of which are difficult to surmount to the person skilled in the art, which has resulted in no DNA vaccine being admitted to testing in clinical phases 2 or 3, so far.

The vaccination of cats with expression constructs to express the genes env and gag is described in the French patent. FR 2 751 223. The invention outlined therein however is purely hypothetical and not disclosed sufficiently; no expression- or immunisation experiments or results thereof are shown. It is a purely speculative application.

Experiments regarding DNA immunisation in the area of FeLV are known (Jarrett et al., 2000 Immunology 101, 120-125), however they did not lead to a convincing result. In this publication, the whole genome comprising a polymerase deletion was inoculated as an expression construct. The clinical success of the vaccination did not go as far as a protection of the cats against infection or viremia. Apart from such practical disadvantage of the cited vaccination experiment, the use of deletion mutants or their genome for vaccination has the disadvantage that the risk remains that novel infectious pathogens arise from recombination of a deleted virus with endogenous or exogenous viral sequences.

In contrary to the cited work by Jarrett, the aim of the efforts leading up to the present invention was to only express isolated FeLV antigens. Preliminary experiments however showed that inoculation of expression constructs that expressed homologous wild type sequences encoding the "env" and "gag" genes of FeLV under control of the cytomegalic virus (CMV) early immediate promoter did not provoke an antibody response in cats. Further experiments also showed that the respective sequences were not expressed, or only to a very small degree, in human and feline cell lines. This phenomenon is known for sequences of the Hi virus and other lentivruses (Wagner et al., 2000, Hum Gene Ther 11(17), 2403-2413). The expression of wild type sequences in the infected cell is thereby dependent on the prior expression of the virally encoded rev protein.

Such expression control is not known for the FeLV virus, which does not belong to the class of lentiviruses, and a mechanism similar to "rev" control has never been demonstrated or postulated in the literature.

It is also known that by optimizing the expression construct's codon usage to the codons that are preferentially used in mammals, the expression of proteins can be significantly increased (Grantham et al., Nucleic Acids Res 1980, 9:1893-912). This method was already employed successfully to raise the expression level of various viral structural proteins of HIV-1 and SIV. The effect relies on the circumvention of "rev" dependent transport mechanisms for the extremely AT-rich transcript of these late proteins in the replication cycle of lentiviruses. Codon optimization of the DNA sequences of the "env" and "gag" protein of the human HI virus leads to far greater antibody titres against these synthetic antigens in mice than was possible for wild type sequences (Haas et al., 1998, J. Virol. 72: 1497-503, Wagner et al., Hum Gene Ther. 2000, 17:2403-13). The synthesis and use of such optimized sequences for vaccination against HIV-1 is also known from WO 00/029561 and WO 97/48370.

Another problem concerns the application of the DNA encoding the immunogenic antigens or parts thereof. A disadvantage of the vectors currently used for DNA transport (transfection) is caused by the fact that either vectors of viral origin are used, which cause problems concerning the aspect of safety (Lehrman, 1999, Nature 401: 517-518), or plasmids are used. Since plasmids are produced by bacterial fermentalon, they contain, apart from the desired gene, also DNA necessary for their propagation and selection and resistance genes against commonly used anibiotics. This problem is discussed in detail in WO 98/21322. It shall be mentioned that when using gene expression constructs on the basis of plasmid DNA, the inherent risk of propagating antibiotic resistance genes is present, which is especially intolerable in large vaccination campaigns.

Covalently closed minimalist DNA constructs such as disclosed in EP 0 914 318 B1 are a different type of DNA vector. Especially their application in the form of peptide-linked DNA constructs leads to a surprising, qualitatively improved immune response in comparison to unmodified DNA (also see DE 101 56 679.4 and DE 101 56 678.6).

Apart from the disadvantages caused by current gene transfer methods, an efficacious and safe vaccine against FeLV has not yet been developed. Until today, the treatment of a FeLV infection is restricted to a boosting of the unspecific defences of the animals and a treatment of secondary accompanying infections. The available vaccines comprise the side effects mentioned earlier.

Departing from this state of the art, it is the objective of the present invention to provide a vaccine, which leads to a protection of cats against infections with FeLV, as well as suitable diagnostic tools. ps Solution of the Problem and Advantages of the Invention.

SUMMARY OF THE INVENTION

According to the invention, the objective is attained by immunizing cats with a mixture (cocktail) from synthetically made DNA sequences that are optimized for codon usage and splicing signals and encode structural proteins "gag" and the most important membrane protein "env" of FeLV.

In the course of optimisation regarding codon and signal usage, mutated sequences were obtained that led to the substitution of single amino acids in the structural proteins ("gag") and the most important membrane protein ("env") of FeLV. Surprisingly, these proteins with changed amino acid sequence provided the inventive advantages. In this regard, the optimisation of codon and signal usage according to the invention is a strategy for changing the amino acid sequence of the structural proteins "gag" and the most important membrane protein "env" of FeLV.

In the context of the invention, the following terms shall mean

"env": Gene sequence encoding the viral coat proteins of the inner viral packaging of feline leukosis virus "gag": Gene sequence encoding the viral structural proteins of the inner viral packaging of feline leukosis virus FeLV: feline leukosis virus WT: wild type WT "env": wild type of the "env" DNA sequence, extracted from the NCBI database, Acc. No. M12500

WT "gag": wild type of the "gag" DNA sequence, derived from the blood of infected cats (see example 1), no database sequence, but homologous to one. [0033] NLS: Nuclear localisation signal sequence ODN: oligodeoxynucleotide PCR: Polymerase Chain Reaction LeadFeLVenv FeLV "env" sequence with signal sequence (FeLVenv):

LeadFeLVenvgp85 FeLV "env" sequence (gp85) with signal sequence (FeLVenvgp85):

The gene sequence "gag" encodes the viral structural proteins of the inner viral packaging, the gene sequence "env" encodes the coat proteins. The protein possessing the highest immunogenicity of all proteins encoded in the "env" sequence is the glycoprotein gp70. Virus neutralising antibodies are being produced in the cat organism against gp70. These antibodies constitute the first immune response after the entry of the pathogen into the body, which can in certain circumstances be sufficient to fight the infection.

Controversy exists whether membrane proteins or secreted proteins are better suited to induce virus neutralising antibodies. For this reason, two different constructs encoding "env" were made. It is known that the p15 sequence of the "env" gene sequence contains at least one sequence tract that has immune modulating properties (Haraguchi et al., 1997, Journal of Leukocyte Biology, 61, 654-666), by which it suppresses antibody formation. Hence, apart from a construct encoding gp70 and p15 (gp85), another construct was made containing only gp70 and leading to the expression of a secreted "env" protein without transmembrane region.

A vaccine that can induce both virus neutralising antibodies against gp70 and a T-cell mediated immune response therefore constitutes a significant improvement in comparison to vaccines available to date, and might be employed also for the therapy of infected cats.

In order to express more antigen in-vivo and to elicit a stronger immune response that results in an effective and long-lasting protection against FeLV infection, the wild type sequences of "gag" and "env" were optimized. Optimization shall embrace both codon adaption and codon usage optimisation.

Every amino acid can be encoded by several codons. The frequency by which any particular codon is read during translation varies very substantially between viruses, bacteria and vertebrates. Accordingly, the occurrence of the respective tRNA in the cell also varies. Viral genomes show a codon usage frequency that partially differs from the host cell, which most probably comprises an element of expression control of the virus. By adapting the sequence to the host-specific codon usage pattern, such viral control mechanisms can be subverted and the expression of antigen can be increased substantially.

For this reason, the objective of the experiments was to attain a much stronger expression of the antigens by editing the viral sequences into sequences that represent a codon usage optimal for vertebrate genomes. A cloning strategy was developed with this objective which enabled the synthesis of such optimised DNA sequence from oligonucleotides.

Synthetic sequences were inserted into plasmids, propagated in *E. coli*, sequenced for control and subsequently transfected into a cat cell line in order to test the expression of the encoded proteins.

The proof of expression of the antigens was performed by Western blots.

The proof of expression of the proteins from the FeLV wild type sequences (WT) "env" and "gag" was performed by Western blot.

Both "env" and "gag" could be shown only as very small bands when assayed by immune precipitation. Surprisingly, this was also the case for the codon optimized "env" sequences. Only with "gag", codon optimization lead to a significantly improved expression, as shown in FIG. 1. After trying many other hypotheses that were meant to explain the dissatisfying expression of the synthetic genes, the synthetic "env" sequence was analysed for sites predicted by bioinformatics methods. A number of such signals predicted by the employed programme (Complign PPC, Mac Molly Tetra Version 3.10a (Softgene GmbH)) was deleted by point mutation, in order to verify the hypothesis that the presence of such structures inhibits the expression of the genes in the context of the promoter used. Surprisingly, it was possibly to demonstrate "env" as a strong protein band in the Western blot by this measure (see FIG. 2). The synthetic antigen sequences according to the invention showed the successful improved expression of the antigens by virtue of the strong bands.

Generally, a connection between the strength of expression of an expression system and the resulting strength of the immune response is postulated, although numerous findings suggest that neither a linear correlation exists, nor that necessarily every treatment with expression vectors confers immunity in the desired strength (Wherry et al., Journal of Immunology 2002, 168 pp 4455-4461). For this reason, once the in-vitro expression results had been obtained, mice were immunised with peptide-linked expression vectors encoding the codon optimized and -signal optimized "env". The advantages of such peptide linked constructs in eliciting an immune response are explained in detail in the disclosures of EP 0 941 318 B1 and DE 101 56 678 A1. In order to determine the immunologic importance of the p15 protein of "env" with regard to the provocation of an immune response, both sequences encoding "env" according to the invention were used (SEQ ID NO: 7, 8, 9 and 10). The sera of immunized mice were assayed for specific antibodies against the FeLV viral protein "env" by means of Western blot. The antibody levels after the second immunization in week 4 clearly demonstrate that the synthetic constructs lead to a strong stimulation of antibody formation in-vivo, as well. In comparison, five of six mice of group 4 showed a strong immune response against the inventive antigen sequence, whereas the WT sequence (group 1) only led to a weak immune response in two of six animals (see FIG. 3).

Plasmids can be used as DNA expression constructs, however according to the invention, minimalist immunologically defined expression constructs are preferred. These are linear, covalently closed expression cassettes that consist only of a CMV promoter, an intron, the respective gene sequence and a polyadenylation sequence. These covalently closed minimalist DNA constructs are referred to as Midge vectors in the following (MIDGE: MINIMALISTIC IMMUNOLOGICALLY DEFINED GENE EXPRESSION VECTOR); see EP 0 941 318 B1. The Midge constructs have the advantage that they allow the avoidance of structures that are not essential for their medical function, thus avoiding the disadvantages of the conventional gene transfer systems.

For transfection, biological, chemical and/or physical methods known in the state of the art can be employed, for instance transfection by ballistic transfer. In a preferred embodiment of the invention the transfection is achieved by intradermal injection by syringes or needle free injection devices.

The invention concerns expression constructs that lead to expression of antigens of FeLV in mammalian cells. The invention thus provides a vaccine that leads to protection from infection with FeLV in cats and considers the aspect of safety. According to the invention, conventional adjuvants are not employed, thus excluding the risk of fibrosarcoma formation at the site of injection.

Further advantageous methods are the biological transfection methods, such as peptide mediated gene transfer. To give an example, a DNA expression construct encoding at least the "env" and the "gag" sequence as provided by this invention, are attached covalently to a peptide, which preferably is the nuclear localisation signal (NLS) of the simian virus 40.

After the positive results in the mouse experiment, cats were immunized with the expression constructs and their antibody status was determined. The attached sequence protocol, which is part of the application and the present disclosure, contains the following sequences:

SEQ ID NO: Sequence name-description
SEQ ID NO: 1 DNA sequence of the "env"-gene wild type
SEQ ID NO: 2 DNA sequence of the "gag" gene wild type
SEQ ID NO: 3 Protein sequence of the "env"-gene wild type
SEQ ID NO: 4 Protein sequence of the "gag" gene wild type
SEQ ID NO: 5 DNA sequence of the mutated "gag" gene
SEQ ID NO: 6 Protein sequence of the mutated "gag" gene
SEQ ID NO: 7 DNA sequence of the mutated "env" gene (gp85). The gp70 sequence is extended here by the sequence encoding the immunogenic p15 protein.
SEQ ID NO: 8 DNA sequence of the mutated "env" gene (gp70)
SEQ ID NO: 9 Protein sequence of the mutated "env" gene (gp85)
SEQ ID NO: 10 Protein sequence of the mutated "env" gene (gp70)
SEQ ID NO: 11 DNA sequence of the wild type of the "env" gene (gp70), derived from SEQ ID NO: 1 (NCBI database, Acc. No. M12500).
SEQ ID NO: 12 to SEQ ID NO: 40 sequences of the primers employed according to the following examples.

According to the invention, a DNA expression construct is provided for the expression of gene products of the feline leukosis virus (FeLV) in cat cells, consisting of a promoter sequence operable in Felidae and at least one nucleotide sequence that is related to a wild type nucleotide sequence encoding an original structural protein ("gag") and/or a membrane protein ("env") of FeLV, wherein said nucleotide sequence of FeLV is mutated and contains no open or hidden donor and/or acceptor sequences or a highly homologous but not identical part thereof. The proteins, which are highly homologous but not identical to the original membrane protein ("env") of FeLV, show a homology to the corresponding wild type of at least 98%. Preferred is an expression construct containing the sequences SEQ ID NO: 5, SEQ ID NO: 7 and/or SEQ ID NO: 8.

The structural or membrane proteins are encoded completely or partially by the corresponding nucleotide sequences. The expression construct is either a plasmid or a construct in which the immunising polynucleotide sequences are in the form of expression constructs comprising a linear double stranded region and the single strands forming said double stranded region are attached to each other by short single stranded loops made of deoxyribonucleotides, and where the single strands forming said double strand only consist of the coding sequence, under control of a promoter sequence operable in the in the vaccinated animal, and a terminator sequence.

For an improved transfection, the expression construct can be attached to one or more peptides covalently. A peptide of 3 to 30 amino acids, at least half of which are taken from the group of arginine and lysine, especially a peptide with the amino acid sequence PKKKRKV (Proline-Lysine-Lysine-Lysine-Arginine-Lysine-Valine), is preferred.

According to the invention, also proteins are provided that are a protein highly homologous to the original structural protein ("gag") of the Feline Leukosis virus (FeLV) (SEQ ID NO: 6) or with the original membrane protein gp85 ("env") of FeLV (SEQ ID NO: 9) or with the original membrane protein gp70 ("env") of FeLV (SEQ ID NO: 10). These proteins in turn can be used for antibody production (monoclonal or polyclonal antibodies), which again in turn can be part of diagnostic kits for the diagnosis of infection of cats with feline leukosis virus.

The expression construct according to the invention is provided as part of a pharmaceutical composition, especially a vaccine for the production of preventive and/or therapeutic immunity in felidae, especially in cats.

Further advantageous embodiments of the invention can be derived from the dependent claims and the description. The surprising effect of the pharmaceutical according to the invention as a vaccine for FeLV therapy and the inventive method is explained by the figures and examples. In this context, the abbreviations shall have the following meanings:

Midge-NLS-FeLVenvgp85(−) or NLS-coupled Midge vector encoding

Midge-NLS-FeLVgp85(−) the codon- and signal optimized "env" sequence with p15 (gp85)

Midge-NLS-FeLVenvgp70(−) or NLS-coupled Midge vector encoding

Midge-NLS-FeLVgp70(−) the codon- and signal optimized "env" sequence without p15 (gp70)

Midge-NLS-WT NLS-coupled Midge vector encoding the WT of the "env" gene mAK vs. gp70Monoclonal antibody against gp70

Positive control Leukogen vaccine

Buffer PBS, negative control

DETAILED DESCRIPTION OF PREFERRED EMBODIMENTS

It is shown in:

FIG. 1: in-vitro comparison of expression of the WT "gag"-protein and the codon optimized "gag" protein. Loaded was lysate from cat cells that previously had been transfected with the following constructs. The "gag" precursor has a size of 55 kD:

Lane 1+2: expression constructs encoding "gag"-WT

Lane 3: expression vectors encoding codon-optimized "gag"

Lane 4: non-infected cat cells, negative control

Lane 5: empty

Lane 6: virus-infected cat cells, positive control

Lane 7: Boa protein marker

Expression by WT leads to very weak protein bands (1 and 2), whereas a strong expression is attained by the sequence according to the invention (3). Infected cat cells served as a comparison (6). "gag" signifies a precursor protein that is cleaved into structural proteins of the FeLV in the infected cell by means of proteases. The strongest immunogen is the structural protein p27, which is thus well recognized by an antiserum against whole virus. This explains why in lane 6, both a band representing the 55 kDa whole "gag" and a 27-kDa band can be recognized. In contrast to this situation, lane 3 does not contain virus particles, but cells transfected with "gag" gene; this apparently does not lead to a degradation of the "gag" gene product into the viral proteins by means of proteases, but to the unspecific degradation of the entire precursor protein by cellular proteases.

FIG. 2: in-vitro comparison of expression of the WT "env" gene and the codon-and-optimized "env" sequence (gp85). Loaded was lysate from cat cells that previously had been transfected with the following constructs:

Lane 1+2: expression constructs encoding "gag"-WT

Lane 3: expression constructs encoding codon optimized "gag"

Lane 4:

Lane 5: empty

Lane 6:

Lane 7: Boa protein marker

Lane 1: Boa protein marker

Lane 2: non-infected cat cells, negative control

Lane 3: virus-infected cat cells, positive control

Lane 4: empty

Lane 5: virus-infected cat cells, precipitate, positive control

Lane 6: non-infected cat cells, precipitate, negative control

Lane 7: further negative controls for specific proof of "env"

Lane 8: empty

Lane 9: expression vectors encoding codon- and signal optimized FeLVenvgp85(−)

Lane 10: empty

Lane 11: expression vectors encoding codon-optimized FeLVenvgp70(−)

The control in lane 5 provides a clear protein band that can be used as a positive control for the expression of envgp85. Lane9 shows that the inventive sequence FeLVenvgp85(−) induces the expression of the gp85 protein. Lane 11 shows the inventive FeLVenvgp70(−). The absence of the 70 kDa band can be explained by the envgp70 being a secreted protein, in contrast to gp85, and thus being difficult to detect, if at all, in the cell lysate.

FIG. 3: in-vivo results after immunisation of mice with expression constructs encoding "env". The abbreviations have the following meaning: [0110] A: Positive control [0111] B: buffer Antibody measurement was performed at week 4 after the second immunisation. In group 3, 3 of 6 mouse sera are antibody positive (gel lanes under the arrow: Midge-NLS-FeLVgp85(−)), in the 4. group, 5 sear test strongly positive and 1 weakly positive (gel lanes under the arrow: Midge- NLS-FeLVgp70(−)). The animals immunized with WT in group 5 however showed very weak positive signals in only two cases (gel lanes under the arrow: Midge-NLS-WT). The experiment demonstrates that the optimized sequences lead to a much improved antibody formation in vivo also, in comparison to the WT sequences, and confirms the results of the in-vitro experiments.

FIG. 4: DNA sequence comparison of the wild type "gag" gene (SEQ ID NO: 2) against the codon-optimized "gag" gene (SEQ ID NO: 5). Similarity: 74.51%

FIG. 5: DNA sequence comparison of the wild type "env" (gp70 region from SEQ ID NO: 1) against the codon- and signal optimized "env" gene (gp70; SEQ ID NO: 8). Similarity: 75.75%

FIG. 6: DNA sequence comparison of the wild type "env" gene (SEQ ID NO: 1) against the codon- and signal optimized "env" gene (gp85) (SEQ ID NO: 7). Similarity: 80.25%

FIG. 7: Protein sequence comparison of the wild type "gag" protein (SEQ ID NO: 4) against the protein sequence of the codon-optimized "gag" protein (SEQ ID NO: 6). Similarity: 98.62%

FIG. 8: Protein sequence comparison of the wild type "env" protein (SEQ ID NO: 3) against the protein sequence of the codon- and signal optimized "env" protein (gp70) (SEQ ID NO: 10). Similarity: 98.75%

FIG. 9: Protein sequence comparison of the wild type "env" protein (SEQ ID NO: 3) against the protein sequence of the codon- and signal optimized "env" protein (gp85) (SEQ ID NO: 9). Similarity: 98.60%

The results show that the codon- and signal optimized DNA sequences both of the "env" and the "gag" gene of FeLV show a homology to the corresponding wild type of at least 74%. From these arise protein sequences of the "env" and "gag" protein of at least 98%. Other optimizations of the DNA sequence of "env" and "gag" of FeLV are conceivable that lead to a similar result, that is a high degree of homology between the original wild type and the protein sequence resulting from the optimisation. Such optimisations are also to be understood to be within the scope of the invention.

Example 1

Wild Type (WT)-Sequences

The wild type sequences of the selected antigens, especially the "gag" gene, were obtained from the blood of infected cats. The DNA sequence of the "env" WT is given in SEQ ID NO: 1 (NCBI data base, Acc. No.: M12500), for the "gag" WT in SEQ ID NO: 2. The corresponding amino acid sequences are given in SEQ ID NO: 3 ("env") and SEQ ID NO: 4 ("gag").

Primer for "gag" WT

In order to remove two Eco31I restriction sites, 3 PCR with the following mutation primers were performed:

```
gag-mut1-rneu (SEQ ID NO: 12):
AATTAAGAGCTCCACGTCTCCCCCCGCTAACAGCAACTGGCG gag-mut2-I (SEQ ID NO: 13):
AATTAAGAGCTCCAGGTCTCCGGGGCTCCGCGGGGCTGCAAGACG gag-mut3-r (SEQ ID NO: 14):
AATTAAGAGCTCCACGTCTCCTTCCCTTTTGTTGTATATCTTTTCTGC gag-mut4-I (SEQ ID NO: 15):
AATTAAGAGCTCCAGGTCTCCGGAAACCCCAGAGGAAAGGGAAGAAAG
```

After ligation of the three sequences thus obtained, a PCR was performed with the primers:

```
Felvgag-I (SEQ ID NO: 16):
CGGATAAGGTACCATGGGCCAAACTATAACTACC

Felvgag-r (SEQ ID NO: 17):
TTCTCAGAGCTCTTAGAGGAGAGTGGAGTTGGCGGGT
```

Primer for "env" WT:

```
envl (SEQ ID NO:. 18):
CGGATAAGGTACCATGGCCAATCCTAGTCCACC envr (SEQ ID NO: 19):
AGTTCTCAGAGCTCTTAGGCTGTTTCAAGGAGGGCTT
```

Example 2

Codon Optimization

The codon usage table for cats was obtained from the codon usage database maintained by the Kazusa DNA research Institute, located in Kisarazu, Japan. For every amino acid of the two WT sequences, the codon used most frequently was employed. The following restrictions to this rule were used: If an amino acid was present more than three times in sequence, from the fourth one onwards, the second most frequent codon was used. This was meant to avoid the sudden extreme depletion of the tRNAs and to assure the efficacy of transcription.

In order to avoid uncontrolled immune stimulatory effects, sequences with a C and immediately following G were avoided. In order to avoid restriction sites for Eco31I, KpnI and SacI, all sequences of the base sequence GAGCTC, GGTACC, GGTCTC and GAGACC were removed by choosing alternative, also frequently used codons.

Example 3

Cloning of FeLVenv

Oligonucleotides of a length between 18 and 28 bases were purchased (TibMolbiol). In total, 51 oligonucleotides were joined by annealing and ligation. The overlap was 4 bases. It was assured that any overlap occurred only once and was not palindromic. Every single oligonucleotide was hybridized strand against antisense strand, by heating the single strands (strand and antisense strand) in kinase buffer to about 80 degC. and then cooling them slowly to room temperature. Afterwards, ATP and polynucleotide kinase (PNK) and oligonucleotides were phosphorylated for one hour. Then, in a first step, oligonucleotides neighbouring each other in the sequence were brought together and ligated (oligonucleotide 1+2, oligonucleotide 3+4). After 1 h of ligation, an aliquot of the ligation reaction of oligonucleotides 1+2 and an aliquot of the ligation reaction of 3+4 was brought together. An aliquot of this last ligation reaction was taken and a PCR with flanking primers was performed. If a PCR product of the expected length was obtained, it was inserted into the TOPO Vector pCR 2.1 by TA cloning and the sequence was verified. This was performed analogously for all other fragments of the complete gene. 4 fragments were obtained. The individual fragments were excised from the plasmid of control insertion by EcoRI and ligated after digestion with Eco31 I. The complete ligation product of correct length was digested with BamHI and SacI and inserted into the similarly prepared vector pMCV1.4 after gel extraction. Subsequently, the sequence was verified by sequencing. The resulting plasmid was designated pMCV1.4-FeLVenv.

Primer sequences for the 4 assembled fragments:

Fragment 1:

```
left primer (SEQ ID NO: 20):
ATATTGGATCCCATGGCCAACCCCTCCC right primer (SEQ ID NO: 21)
ATTATGGTCTCCTGCTGCTTCTTCCTGTCTGTGG
```

Fragment 2:

```
left primer (SEQ ID NO: 22):
TAATAGGTCTCCAGCAGCAGACCTACCCCT right primer (SEQ ID NO: 23):
TAATAGGTCTCTGTGAACAGGGCAATGGGGTCA
```

Fragment 3:

```
left primer (SEQ ID NO: 24):
TATTTGGTCTCTTCACAGTGTCCAGGCAGGTGTC right primer (SEQ ID NO: 25):
ATTAGGTCTCAGCTTGTGCTGGGGGGTGG
```

Fragment 4:

```
left primer (SEQ ID NO: 26):
AATAAGGTCTCCAAGCTGACCATCTCTGAGGTGT right primer (SEQ ID NO: 27):
ATTAAGAGCTCTCAGGCTGTTTCCAGC
```

Total Sequence:

```
left primer (SEQ ID NO: 20):
ATATTGGATCCCATGGCCAACCCCTCCC right primer (SEQ ID NO: 27):
ATTAAGAGCTCTCAGGCTGTTTCCAGC
```

Example 4

Cloning Strategy for LeadFeLVenv

For successful processing of the "env2 protein, a signal sequence (leader sequence) was inserted in front of the codon optimized "env" sequence. This signal sequence was assembled from a total of 8 ODN with a length of between 22 to 30 bp by annealing and ligation. From the last ligation step, a PCR was performed for amplification of the leader sequence.

Primer Sequences for the Complete Signal Sequence:

```
left primer (SEQ ID NO: 28):
ATTGCCGGTACCATGGAGTCCCCCACCCACC right primer (SEQ ID NO: 29):
ATCAGAGGTCTCCCATGCCAATGTCAATGGTGAAC
```

At the 3'-end of the PCR product, an Eco31I recognition sequence was generated, which led to an overhanging end after digestion that was reverse complementary to the 5' end of an overhang generated by a similar digestion of the following PCR product.

PCR for FeLVenv:

On the 5' end of the sequence, an Eco31I recognition sequence was generated.

Employed Primer Sequences:

```
left primer (SEQ ID NO: 30):
GATCTGGGTCTCCATGGCCAACCCCTC right primer (SEQ ID NO: 27):
ATTAAGAGCTCTCAGGCTGTTTCCAGC
```

After digestion of the two PCR products with Eco31I, these were purified and ligated to each other. The ligation product was further processed in a PCR, in which a recognition sequence was generated for KpnI at the 5'-end and for SacI at the 3'-end.

Employed Primer Sequences:

```
left primer (SEQ ID NO: 28):
ATTGCCGGTACCATGGAGTCCCCCACCCACC right primer (SEQ ID NO: 27):
ATTAAGAGCTCTCAGGCTGTTTCCAGC
```

The PCR product was digested with KpnI and SacI and inserted into the similarly digested vector pMCV1.4. The resulting plasmid was denominated pMCV1.4-LeadFeL-Venv.

Example 5

Cloning Strategy for LeadFeLVenvgp85

The complete "env" polyprotein consisting of gp70 and p15 was cloned. To this end, the p15 WT sequence was amplified by PCR from the plasmid pMCV1.4-FeLVenvp15 and inserted behind the pMCV1.4-LeadFeLVenv as above mentioned above.

In the amplification of the p15 an Eco31I recognition sequence was generated at the 5'-end.

1. PCR:

Employed Primer Sequences:

```
left primer (SEQ ID NO: 31):
AATTATGGTCTCGCAGTTCAGACAACTACAAATGGC right primer (SEQ ID NO: 32):
AATTATGAGCTCTCAGGGCCTGTCAGGGTC
```

2. PCR:

The sequence of LeadFeLVenv was amplified. Thereby, a recognition sequence was generated at the 3'-end.

Employed Primer Sequences:

```
left primer (SEQ ID NO: 33):
AATTATGGTACCATGGAGTCCCCCACCC right primer (SEQ ID NO: 34):
TATAATGGTCTCAACTGGGCTGTTTCCAGCAGGGC
```

After digestion of the two PCR products with Eco31I these were ligated to each other. The ligation product was processed in a PCR with the following primer sequences:

```
left primer (SEQ ID NO: 33):
AATTATGGTACCATGGAGTCCCCCACCC right primer (SEQ ID NO: 32):
AATTATGAGCTCTCAGGGCCTGTCAGGGTC
```

At the 5' end, a KpnI recognition sequence was thus generated, and a SacI recognition site at the 3' end. After digestion of the PCR product with KpnI and SacI, it was ligated into the similarly digested pMCV1.4 and cloned. The resulting plasmid was designated pMCV1.4-LeadFeLVenvgp85.

Example 6

Splice-Signal Optimization of LeadFeLVenvgp85 (-Splice)

The DNA sequence of LeadFeLVenv was analysed for possible splice signal sequences (sites) Between bases 100 and 140, a site was recognized with 97% probability. After exchanging of base 119 (A to G, amino acid exchange from Gin to Arg), no more potential sites were recognized (lower threshold=40% probability). The generation and cloning of the mutated sequence was performed as follows:

PCR for the Generation of the Mutated Sequence:

First, a fragment (1) was amplified by means of PCR, consisting of bases 1-123 of LeadsynFeLVenv. The forward primer employed generates the recognition sequence for the restriction enzyme KpnI at the 5' end of the PCR product.

The sequence of the reverse primer was chosen so that the PCR product contained the mutation (base 119=G). Additionally, the PCR generated the recognition site of the restriction enzyme Eco31I at the 3'-end of the PCR product. Generally, Eco31I generates a 4 base 5' overhang of the bases 2-5 downstream of the recognition sequence.

The 4-base 5'-overhang generated by digestion of the PCR product by Eco31I at the end of fragment 1 corresponds to bases 120-123 of the sequence of LeadFeLVenv. This sequence in turn corresponds to the overhang generated by digesting LeadFeLVenv with the restriction enzyme BgLII, since bases 119-124 of LeadFeLVenv constiute the recognition site of BgLII.

Bases 1-123 are excised from the construct pMCV1.4-LeadFeLVenv by KpnI and BgLII.

After digestion of the PCR product fragment 1 (with mutation of the base 119=G) with KpnI and Eco31I, this can be ligated and cloned into the vector pMCV1.4-LeadFeLVenv, which had previously been digested with KpnI and BgLII, and purified. The resulting plasmid was designated pMCV1.4-FeLVenvgp70(-splice).

Employed Primer Sequences:

```
left primer (SEQ ID NO: 28):
5'-ATTGCCGGTACCATGGAGTCCCCCACCCACC right primer (SEQ ID NO: 35):
5'-ATATTAGGTCTCAGATCCGGGGGGGGGAGGG
```

Analogously, the PCR product fragment 1 was ligated cloned into the vector pMCV1.4-LeadFeLVenvgp85(-splice) which had previously been digested with KpnI and BgLII, and purified. The resulting plasmid was designated pMCV1.4-FeLVenvgp85(-splice).

Example 7

Cloning Strategy for FeLVgag

Cloning of FeLVgag was performed analogously to the process described under 3. The sequence was produced by annealing and ligating oligonucleotides to three single fragments. The sequence was assembled from a total of 2.times.31 oligonucleotides (forward and reverse strand). The fragments were used as templates in a PCR and amplified with the following primer sequences:

Fragment 1:

```
left primer (SEQ ID NO: 36):
ATATTGGTCTCAGGAGAGGGACAAGAAGAG right primer (SEQ ID NO: 37):
AATATGGTCTCTCAGCCTGCTGGCGATGGGGC
```

Fragment 2:

```
left primer (SEQ ID NO: 38):
ATTATGGTCTCTGCACCTGAGGCTGTACAGGC right primer (SEQ ID NO: 39):
AATATGGTCTCGGTGCTCCCTGCCGGCGGGGGTGCA
```

Fragment 3:

```
left primer (SEQ ID NO: 38):
ATTATGGTCTCTGCACCTGAGGCTGTACAGGC right primer (SEQ ID NO: 40):
AATATGGTCTCTCTCCTCCTGCCTCTGC
```

Primer for the complete fragment:

```
left primer (SEQ ID NO: 36):
ATATTGGTCTCAGGAGAGGGACAAGAAGAG right primer (SEQ ID NO: 40):
AATATGGTCTCTCTCCTCCTGCCTCTGC
```

Fragment 1, 2 and 3 were cloned into the TOPO-Vector pCR 2.1.intermediately, digested subsequently with Eco 31 I and extracted. The ligation product from 1, 2 and 3 was digested with KpnI and SacI and cloned into pCMV1.4. The resulting plasmid was designatedpCMV1.4-FeLVgag.

Example 7

Transfection of Cells, Proof of Expression

Feline cells of the f3201 cell line were transfected with the plasmids pMCV1.4-FeLVenvgp85(-splice), pMCV1.4-FeLVenvgp70(-splice), FeLVgag and the WT containing plasmids pMOK for "env" and "gag" by means of electroporation at 250 V and 1050.mu.F.

The expression of proteins was demonstrated by the Western blot method. Monoclonal mouse antibodies were employed in the assay. Positive control: FeLV A infected cells of the f3201 cell line.

Example 8

Production of Peptide-Linked Midge

The plasmids pMCV1.4-FeLVenvgp85(-splice), pMCV1.4-FeLVenvgp70(-splice) and pMCV1.4-FeLVgag were digested to completion with the restriction enzyme Eco31I overnight at 37.degree. C. Two DNA fragments were generated by the restriction digest. One consisted of the kanamycin resistance gene, and other sequences necessary for the propagation of the plasmid in bacteria. The other fragment consisted of the sequences that were to be part of the MIDGE-DNA: enhanced CMV-Promoter, chimeric Intron, the corresponding gene sequence and the polyadenylation sequence of SV40.

5'-phosphorylated hairpin oligonucleotides (TIBMolBiol, Berlin) 5'-PH-GGGAGTCCAGT xT TTCTGGAC-3' and 5'PH-AGG GGT CCA GTT TTC TGG AC-3 were ligated to the MIDGE-forming DNA fragment by means of the enzyme T4-DNA-Ligase in the presence of the restriction enzyme Eco31 I overnight at 37.degree. C. The reaction was stopped by heating to 70.degree. C. The resulting mix of nucleic acids was treated with the enzyme T7-DNA-Polymerase. The Midge DNA was purified by anion exchange chromatography and precipitated by isopropanol (see EP 0 941 318 B1).

Production of the Peptide-Linked ODN:

The NLS peptide PKKKRKV (SEQ ID NO: 41) was linked to the ODN in two steps. Firstly, the modified oligonucleotide was activated by sulfo-KMUS (5 mM) in PBS at room temperature (RT). The reaction was stopped by adding 50 mM Tris-(Hydroxymethyl)-Aminomethane after 120 min, and the activated ODN was obtained after ethanol precipitation (300 mM NaOAc pH 5.2, 5.5 mM $MgCl_2$, 70% Ethanol), centrifugation and a single wash with 70% ethanol. The ODN (0.1 mM) thus obtained was dissolved in PBS and reacted with the peptide (0.2 mM) for one hour at room temperature. The reaction was checked by gel electrophoresis (3%) and ethidium bromide staining. The resulting NLS-linked ODN was purified by HPLC and used for the synthesis of the MIDGE-NLS-constructs as described above.

Example 9

Antibody Assay in Mice

Five vaccination groups at six BALB/c mice each were formed (see table 1). The basic antigen in all groups (except the control groups) were the optimized sequences of the "env" protein with and without the immune modulating protein p15. The coding sequence and the cytomegalic virus promoter (CMV) preceding the sequences are employed as linear double stranded molecules according to example 8. As controls, buffer, the common vaccine (Leukogen) and the WT of the "env" protein were employed. After the first immunisation (50.mu.g DNA, 1 i.d.), a second immunisation (boost) was performed on the 15.sup.th day. Blood was taken on days 14, 28 and 42. The blood samples were assayed for specific antibodies against "env".

TABLE 1

Composition of vaccinee groups

| Gr. | Mice | Antigen used | Function |
|---|---|---|---|
| 1 | 6 | Leukogen | Positive control |
| 2 | 6 | PBS buffer | Negative control |

TABLE 1-continued

Composition of vaccinee groups

| Gr. | Mice | Antigen used | Function |
|---|---|---|---|
| 3 | 6 | FeLVenvgp85(-splice) | Determine antibodies |
| 4 | 6 | FeLVenvgp70(-splice) | Determine antibodies |
| 5 | 6 | WT "env" | Positive control |

Figure 3:
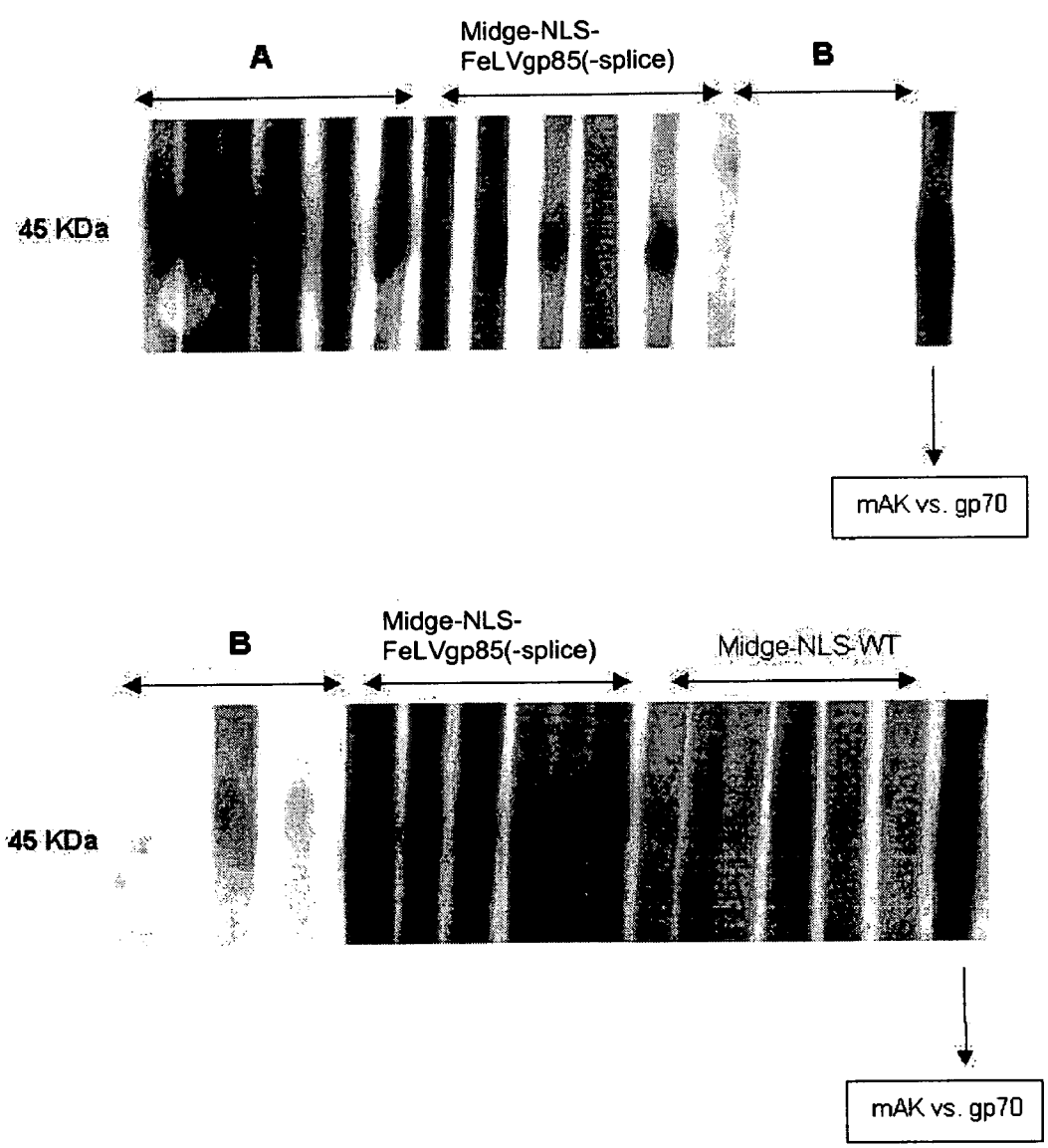

The results are shown in FIG. 3.

Example 10a

Immunisation of Cats

In order to determine whether the synthetic sequences are able to elicit a humoral and cellular immune response in cats, the following vaccination regime was formulated (table 2):

TABLE 2

Composition of vaccinee groups

| Gr. | Cats | Antigen used | Function |
|---|---|---|---|
| 1 | 5 | FeLVenvgp85(-splice) FeLVgag | Determine antibody and cytokine status |
| 2 | 5 | FeLVenvgp70(-splice) FeLVgag | Determine antibody and cytokine status, comparison to group 1 |
| 3 | 2 | PBS Puffer | Negative control |
| 4 | 3 | Leukogen | Positive control |

Cats of the first two groups are immunized twice with a total of 600.mu.g DNA each, dissolved in PBS buffer. The peptide-linked expression constructs are applied by intradermal injection into the neck. The immune response is followed over 12 weeks, The secondary immunisation was performed in week 4. From determining the cytokine status from weekly sampled blood samples, clues about the direction of the immune response (Th1, Th2) shall be derived. IL-4 was deemed to be an indicator of a TH2 response; IL-2 and Interferon-gamma were deemed to be indicators of a predominantly TH1 immune response. The vaccine Leukogen contains recombinant "env" protein and is used as a positive control.

Antibodies against the employed antigens were determined by means of Western blot and ELISA.

The amount of mRNA encoding the cytokines IL-2, IL-4 and Interfero-gamma was determined by means of real-time PCR.

Example 10b

In Vivo Results after Immunisation of Cats According to the Vaccine Regime Described in Table 2

Semi-quantitative assay of antibodies against the "env" protein was performed by means of Western blot. Plasma samples of cats from experimental week 0 and 12 were tested. In week 0, no antibodies against "env" could be found, according to expectations. The weak bands mentioned in table 3 as (+) are unspecific. In week 12, all animals of groups 1, 2 and 4, with the exception of one cat, showed a clear antibody response. These results in the patient animal corroborate those of the pre-experiment in mice (see Example 9).

Herein signify: +++ very strong band,
++ strong band,
+ visible band,
(+) weak band.

The strength of the bands represent the concentration of the antibodies in the plasma of the immunized cats.

TABLE 3

Determination of the humoral immune response against the FeLV protein

| Gr. | Employed antigen | cats | Week 0 | Week 12 |
|---|---|---|---|---|
| 1 | FeLVenvgp85(−) FeLVgag | 1 | − | +++ |
|   |   | 2 | − | ++ |
|   |   | 3 | − | ++ |
|   |   | 4 | − | ++ |
|   |   | 5 | − | ++ |
| 2 | FeLVenvgp70(−) FeLVgag | 1 | − | +++ |
|   |   | 2 | (+) | +++ |
|   |   | 3 | − | ++ |
|   |   | 4 | − | ++ |
|   |   | 5 | − | + |
| 3 | PBS buffer | 1 | (+) | − |
|   |   | 2 | (+) | (+) |
| 4 | Leukogen | 1 | − | +++ |
|   |   | 2 | − | +++ |
|   |   | 3 | − | (+) |

Example 11

Infection as Control of the Protection Conferred by Vaccination

In order to control whether the attained high antibody production is really conferring protection against infection by FeL-Virus, and thus to check the efficacy of the vaccine according to the invention, an experiment with infection followed. Four groups of 10 cats each were vaccinated twice (day 0 and day 21) with the respective constructs intradermally with a needle-free injection device (table 4). As expression constructs, NLS peptide-linked Midge vectors were used. On day 21, 22 and 23 after the last vaccination, cats were infected by a trial infection with live virus (Rickard strain, >10e6 focus-forming units/ml). The efficacy of the vaccine was determined according to whether the cats were protected after the trial infection. Cats were deemed protected if they had no virus particles in their blood (seronegative cats) and no viral DNA in their blood cells. In order to assay the virus particles, cat serum was tested for presence of antigen p27 by ELISA. The amount of integrated viral DNA, the so-called proviral DNA, was assayed by Taqman PCR. The following vaccination regime was formulated:

TABLE 4

| Gr. | Antigen employed | DNA-Doses [μg] | Number of seronegative cats 105 days after trial infection |
|---|---|---|---|
| 1 | PBS buffer | — | 0 |
| 2 | FeLVgag | 2 × 100 | 2 |
| 3 | FeLVenvgp70(-splice) | 2 × 50 | 4 |

PBS buffer was used as negative control.

The results can be summarised as follows:

Table 4 shows the results of the serum assay of the cats regarding the presence of virus protein p27. This test is a generally accepted assay for the diagnosis of FeLV viremia. In parallel, white blood cells of the same cats were analysed for the presence of proviral DNA (data not shown). All virus protein-free cats were also free of proviral DNA.

Since the two test systems determine different steps of the viral development in the body, the twofold negative result indicates that the virus was not able to multiply in the animals' bodies, which is equivalent to protection.

In groups 2 and 3, some of the cats could be protected against the infection with FeLV.

In group 2, 2 of 10 cats were free both of virus protein and of proviral DNA. This vaccine protection was based on the application of the inventive vaccine (SEQ ID NO: 5).

In group 3, 40% of the animals could be protected by the inventive vaccine (SEQ ID NO: 8) against infection with the FeL-Virus. This is a significant reduction of infected cats in comparison to group 1.

In the animals, neither viral protein nor proviral DNA could be detected in the serum and blood samples. It is notable that in order to attain protection in the 4 cats of group 3, the very small dose of 50.mu.g per injection was sufficient in order to protect the cats. That is of advantage since the DNA concentration to be applied is small and hence, the production costs of the vaccine are decreased rapidly.

All animals of group 1(control group) showed viral particles in their blood, i.e. they were not protected and fully receptive for the trial infection.

During the entire immunization experiment, neither side effects in the form of local irritations at the sites of injection, nor disturbances in the general state of well-being of the experimental animals were observed.

What is claimed is:

1. An isolated nucleic acid molecule, or the complement thereof, wherein the isolated nucleic acid molecule comprises the sequence set forth in SEQ ID NO: 5.

2. An isolated nucleic acid molecule, or the complement thereof, wherein the isolated nucleic acid molecule comprises the sequence set forth in SEQ ID NO: 7.

3. An isolated nucleic acid molecule, or the complement thereof, wherein the isolated nucleic acid molecule comprises the sequence set forth in SEQ ID NO: 8.

4. A DNA expression construct for the expression of proteins in the Feline Leucosis virus in cat cells comprising:
a promoter sequence operable in Felidae and at least one Feline Leucosis virus nucleotide sequence which is codon optimized for gene expression in Felidae and contains no splice donor or acceptor sequences, wherein said mutated nucleotide sequence, encodes one of a structure protein "gag" or a membrane protein "env", selected from the group consisting of SEQ ID NO: 5, SEQ ID NO: 7 and SEQ ID NO: 8; and a termination sequence.

5. The DNA expression construct according to claim 4, said construct comprising covalently closed linear deoxyribonucleotide molecules comprising a linear double stranded region, wherein ends of the double stranded region are linked to short single stranded loops consisting of deoxyribonucleotides, said double strand forming single strands consisting only of encoding sequences under the control of the promoter and the terminator sequence operable in an animal to be vaccinated.

6. The DNA expression construct according to claim 4, wherein the expression construct is covalently linked to one or more peptides.

7. The DNA expression construct according to claim 6, wherein the peptide is composed of 30 amino acids, at least half of which are a member of the group consisting of arginine and lysine.

8. The DNA expression construct according to claim 6, wherein the one peptide comprises SEQ ID NO: 41.

9. The DNA expression construct of claim 4 comprising: an isolated nucleic acid molecule, or the complement thereof, wherein the isolated nucleic acid molecule comprises the sequence set forth in SEQ ID NO: 5.

10. A DNA expression construct comprising: an isolated nucleic acid molecule or the complement thereof, wherein the isolated nucleic acid molecule comprises the sequence set forth in SEQ ID NO: 5; wherein the expression of the construct in cat cells provides protection from Feline Leucosis virus infection.

11. The DNA expression construct of claim 4, comprising: an isolated nucleic acid molecule, or the complement thereof, wherein the isolated nucleic acid molecule comprises the sequence set forth in SEQ ID NO: 7.

12. A DNA expression construct comprising: an isolated nucleic acid molecule, or the complement thereof, wherein the isolated nucleic acid molecule comprises the sequence set forth in SEQ ID NO: 7; wherein the expression of the construct in cat cells provides protection from Feline Leucosis virus infection.

13. The DNA expression construct of claim 4, comprising: an isolated nucleic acid molecule, or the complement thereof, wherein the isolated nucleic acid molecule comprises the sequence set forth in SEQ ID NO: 8.

14. A DNA expression construct comprising: an isolated nucleic acid molecule or the complement thereof, wherein the isolated nucleic acid molecule comprises the sequence set forth in SEQ ID NO: 8; wherein the expression of the construct in cat cells provides protection from Feline Leucosis virus infection.

15. The DNA expression construct according to claim 9, further comprising a covalently closed linear deoxyribonucleotide molecule comprising a linear double stranded region, a short single stranded loop consisting of deoxyribonucleotides, a promoter that is operable in an animal that is to be vaccinated, and a terminator sequence.

16. The isolated nucleic acid of claim 1, wherein a "gag" coding sequence is amplified by primers selected from the group consisting of SEQ ID NOS: 36, 37, 38, 39 and 40.

17. A pharmaceutical composition for use as vaccine in comprising a DNA expression construct according to claim 4, and a pharmaceutically effective carrier.

18. A DNA expression construct comprising: a covalently closed linear deoxyribonucleotide molecule comprising a linear double stranded region, wherein ends of the double stranded region are linked to short single stranded loops consisting of deoxyribonucleotides, said double strand forming single strands consisting of at least one Feline Leucosis mutated virus nucleotide sequence, and a promoter sequence operable in Felidae, wherein the mutated nucleic acid comprises a sequence selected from the group consisting of SEQ ID NO: 5, SEQ ID NO: 7 and SEQ ID NO: 8; and a termination sequence.

19. An isolated nucleic acid molecule, or the complement thereof comprising the sequence set forth in SEQ ID NO: 7, wherein a 'env-gp85" coding sequence is amplified by primers which selectively hybridize to the same sequence of SEQ ID No. 7.

20. An isolated nucleic acid molecule or the complement thereof comprising the sequence set forth in SEQ ID NO: 8, wherein a 'env-gp70' coding sequence is amplified by primers which selectively hybridize to the same sequence of SEQ ID No. 8.

* * * * *

SEQUENCE LISTING

```
<160> NUMBER OF SEQ ID NOS: 41

<210> SEQ ID NO 1
<211> LENGTH: 1929
<212> TYPE: DNA
<213> ORGANISM: Feline leukemia virus
<220> FEATURE:
<221> NAME/KEY: gene
<222> LOCATION: (1)..(1929)
<223> OTHER INFORMATION: DNA sequence wild type "env" gene without
      signal peptide coding region
<300> PUBLICATION INFORMATION:
<308> DATABASE ACCESSION NUMBER: NCBI M12500
<309> DATABASE ENTRY DATE: 2001-02-21
<313> RELEVANT RESIDUES IN SEQ ID NO: (162)..(1990)

<400> SEQUENCE: 1
atggaaagtc caacgcaccc aaaaccctct aaagataaga ctctctcgtg gaacttagcg    60
```

```
tttctggtgg ggatcttatt tacaatagac ataggaatgg ccaatcctag tccacaccaa      120
atatataatg taacttgggt aataaccaat gtacaaacta cacccaagc taacgccacc       180 tctatgttag gaaccttaac cgatgcctac cctaccctac atgttgactt atgtgaccta      240
gtgggagaca cctgggaacc tatagtccta aacccaacca atgtaaaaca cggggcacgt     300
tactcctcct caaaatatgg atgtaaaact acagatagaa aaaaacagca acagacatac     360 ccctttacg tctgccccgg acatgccccc tcgttgggc caagggaac acattgtgga        420 ggggcacaag atgggttttg tgccgcatgg ggatgtgaga ccaccggaga agcttggtgg     480
aagcccacct cctcatggga ctatatcaca gtaaaaagag ggagtagtca ggacaatagc    540
tgtgagggaa aatgcaaccc cctggttttg cagttcaccc agaagggaag acaagcctct    600
tgggacggac ctaagatgtg gggattgcga ctataccgta caggatatga ccctatcgct   660
ttattcacgg tgtcccggca ggtatcaacc attacgccgc ctcaggcaat gggaccaaac  720
ctagtcttac ctgatcaaaa accccatcc cgacaatctc aaacagggtc caaagtggcg   780
acccagaggc cccaaacgaa tgaaagcgcc ccaaggtctg ttgccccac caccatgggt     840 cccaaacgga ttgggaccgg agataggtta ataaatttag tacaagggac ataccctagcc  900 ttaaatgcca ccgaccccaa caaaactaaa gactgttggc tctgcctggt ttctcgacca   960
ccctattacg aagggattgc aatcttaggt aactacagca accaaacaaa ccccccccca  1020
tcctgcctat ctactccgca acacaaacta actatatctg aagtatcagg gcaaggaatg  1080
tgcataggga ctgttcctaa aacccaccag gctttgtgca ataagacaca cagggacat   1140 acaggggcgc actatctagc cgcccccaac ggcacctatt gggcctgtaa cactggactc  1200
accccatgca tttccatggc ggtgctcaat tggacctctg attttttgtgt cttaatcgaa  1260 ttatggccca gagtgactta ccatcaaccc gaatatgtgt acacacattt tgccaaagct  1320
gtcaggttcc gaagagaacc aatatcacta acggttgccc ttatgttggg aggacttact  1380 gtaggggca tagccgcggg ggtcggaaca gggactaaag ccctccttga aacagcccag  1440
ttcagacaac tacaaatggc catgcacaca gacatccagg ccctagaaga atcaattagt  1500
gccttagaaa agtccctgac ctccctttct gaagtagtct tacaaaacag acggggccta  1560
gatattctat tcttacaaga gggagggctc tgtgccgcat tgaaagaaga atgttgcttc  1620
tatgcggatc acaccggact cgtccgagac aatatggcca aattaagaga aagactaaaa  1680
cagcggcaac aactgtttga ctcccaacag ggatggtttg aaggatggtt caacaagtcc  1740
ccctggttta caaccctaat ttcctccatt atgggcccct tactaatcct actcctaatt  1800
ctcctcttcg gccatgcat ccttaaccga ttagtacaat cgtaaaaga cagaatatct   1860 gtggtacagg ctttaatttt aacccaacag taccaacaga taaagcaata cgatccggac  1920
cgaccatga                                                         1929
```

<210> SEQ ID NO 2
<211> LENGTH: 1527
<212> TYPE: DNA
<213> ORGANISM: Feline leukemia virus
<220> FEATURE:
<221> NAME/KEY: gene
<222> LOCATION: (1)..(1527)
<223> OTHER INFORMATION: DNA sequence wild type "gag" gene

<400> SEQUENCE: 2

```
atgggccaaa ctataactac ccccttgagc ctcaccctca accactggtc tgaggttcag    60
gcacgggccc gtaatcaggg tgtcgaagtc cggaaaaaga aatggattac actgtgtgaa   120
```

```
gccgaatggg taatgatgaa tgtaggttgg ccccgagaag gaactttcac cattgacaat    180
atttcacagg tcgaggagag aatcttcgcc ccggggccat atggacaccc agatcaaatc    240
ccttatatta ccacgtggag atccctagcc acagaccccc ctccatgggt tcgcccattc    300 ctacccccctc ctaagcatcc caggacagat cctcccgagc ctctttcgcc gcaacctctt    360
gcgccgcaac cctcttcccc ccaccccgtc tctacccccg ttctccccaa ccagaccccc    420
cccaaggcgc ctgtattacc acccaatcct tcttcccctt taattgatct cttaacagaa    480
gagccacctc cctatcctgg gggtcacggg ccaacaccgc cgtcaggccc tagaacccca    540
actgcctccc cgattgccat ccggctgcga gaacgacgag aaaatccagc tgagaaatct    600
caagccctcc ccttaaggga agacccaaac aacagacccc agtactggcc attctcggcc    660
tctgacctgt acaattggaa attgcataac ccccctttct cccaggaccc agtggcccta    720
actaacctaa ttgagtccat tttagtgaca catcagccaa cctgggacga ctgccaacag    780
ctcttacagg ctctcctgac ggcagaggag agacaaaggg tcctccttga agcccgaaag    840
caagttccag gcgaggacgg acggccaacc cagctgccca atgtcgttga cgaggctttc    900
cccttgaccc gtcccaactg ggattttttgt acgccggcag gtaggagca cctacgcctt    960 tatcgccagt tgctgttagc ggggctccgc ggggctgcaa gacgccccac taatttggca   1020
caggtaaagc aagttgtaca agggaaagag gaaacgccag cctcattctt agaaagatta   1080
aaagaggctt acagaatgta tactccctat gaccctgagg acccagggca ggctgctagt   1140
gttatcctgt ccttttatcta ccagtctagc ccggacataa gaataagtt acaaaggcta   1200 gaaggcctac aggggttcac actgtctgat ttgctaaaag aggcagaaaa gatatacaac   1260
aaaagggaaa ccccagagga aagggaagaa agattatggc agcggcagga agaaagagat   1320
aaaaagcgcc ataaggagat gactaaagtt ctggccacag tagttgctca gaatagagat   1380
aaggatagag gggaaagtaa actgggagat caaaggaaaa tacctctggg gaaagaccag   1440
tgtgcctatt gcaaggaaaa gggacattgg gttcgcgatt gcccgaaacg acccccggaag   1500 aaacccgcca actccactct cctctaa                                       1527
```

<210> SEQ ID NO 3
<211> LENGTH: 642
<212> TYPE: PRT
<213> ORGANISM: Feline leukemia virus
<220> FEATURE:
<221> NAME/KEY: PEPTIDE
<222> LOCATION: (1)..(447)
<223> OTHER INFORMATION: Amino acid sequence of the protein
      corresponding to Seq.ID1

<400> SEQUENCE: 3

Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

-continued

```
His Gly Ala Arg Tyr Ser Ser Lys Tyr Gly Cys Lys Thr Thr Asp
            100                 105                 110

Arg Lys Lys Gln Gln Thr Tyr Pro Phe Tyr Val Cys Pro Gly His
            115                 120                 125

Ala Pro Ser Leu Gly Pro Lys Gly Thr His Cys Gly Gly Ala Gln Asp
130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
            195                 200                 205

Leu Arg Leu Tyr Arg Thr Gly Tyr Asp Pro Ile Ala Leu Phe Thr Val
            210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
            275                 280                 285

Arg Leu Ile Asn Leu Val Gln Gly Thr Tyr Leu Ala Leu Asn Ala Thr
290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
            355                 360                 365

His Gln Ala Leu Cys Asn Lys Thr Gln Gln Gly His Thr Gly Ala His
            370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
            435                 440                 445

Ser Leu Thr Val Ala Leu Met Leu Gly Gly Leu Thr Val Gly Gly Ile
450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
            515                 520                 525
```

```
Gly Leu Cys Ala Ala Leu Lys Glu Cys Cys Phe Tyr Ala Asp His
            530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
            595                 600                 605

Asn Arg Leu Val Gln Phe Val Lys Asp Arg Ile Ser Val Val Gln Ala
            610                 615                 620

Leu Ile Leu Thr Gln Gln Tyr Gln Gln Ile Lys Gln Tyr Asp Pro Asp
625                 630                 635                 640

Arg Pro

<210> SEQ ID NO 4
<211> LENGTH: 508
<212> TYPE: PRT
<213> ORGANISM: Feline leukemia virus
<220> FEATURE:
<221> NAME/KEY: PEPTIDE
<222> LOCATION: (1)..(508)
<223> OTHER INFORMATION: Amino acid sequence of the protein
      corresponding to Seq.ID2

<400> SEQUENCE: 4

Met Gly Gln Thr Ile Thr Thr Pro Leu Ser Leu Thr Leu Asn His Trp
1               5                   10                  15

Ser Glu Val Gln Ala Arg Ala Arg Asn Gln Gly Val Glu Val Arg Lys
                20                  25                  30

Lys Lys Trp Ile Thr Leu Cys Glu Ala Glu Trp Val Met Met Asn Val
            35                  40                  45

Gly Trp Pro Arg Glu Gly Thr Phe Thr Ile Asp Asn Ile Ser Gln Val
        50                  55                  60

Glu Glu Arg Ile Phe Ala Pro Gly Pro Tyr Gly His Pro Asp Gln Ile
65                  70                  75                  80

Pro Tyr Ile Thr Thr Trp Arg Ser Leu Ala Thr Asp Pro Pro Pro Trp
                85                  90                  95

Val Arg Pro Phe Leu Pro Pro Lys His Pro Arg Thr Asp Pro Pro
                100                 105                 110

Glu Pro Leu Ser Pro Gln Pro Leu Ala Pro Gln Pro Ser Ser Pro His
            115                 120                 125

Pro Val Leu Tyr Pro Val Leu Pro Lys Pro Asp Pro Pro Lys Ala Pro
            130                 135                 140

Val Leu Pro Pro Asn Pro Ser Ser Pro Leu Ile Asp Leu Leu Thr Glu
145                 150                 155                 160

Glu Pro Pro Pro Tyr Pro Gly Gly His Gly Pro Thr Pro Pro Ser Gly
                165                 170                 175

Pro Arg Thr Pro Thr Ala Ser Pro Ile Ala Ile Arg Leu Arg Glu Arg
            180                 185                 190

Arg Glu Asn Pro Ala Glu Lys Ser Gln Ala Leu Pro Leu Arg Glu Asp
            195                 200                 205

Pro Asn Asn Arg Pro Gln Tyr Trp Pro Phe Ser Ala Ser Asp Leu Tyr
            210                 215                 220

Asn Trp Lys Leu His Asn Pro Pro Phe Ser Gln Asp Pro Val Ala Leu
```

```
225                 230                 235                 240
Thr Asn Leu Ile Glu Ser Ile Leu Val Thr His Gln Pro Thr Trp Asp
                245                 250                 255
Asp Cys Gln Gln Leu Leu Gln Ala Leu Leu Thr Ala Glu Glu Arg Gln
            260                 265                 270
Arg Val Leu Leu Glu Ala Arg Lys Gln Val Pro Gly Glu Asp Gly Arg
        275                 280                 285
Pro Thr Gln Leu Pro Asn Val Val Asp Glu Ala Phe Pro Leu Thr Arg
    290                 295                 300
Pro Asn Trp Asp Phe Cys Thr Pro Ala Gly Arg Glu His Leu Arg Leu
305                 310                 315                 320
Tyr Arg Gln Leu Leu Leu Ala Gly Leu Arg Gly Ala Ala Arg Arg Pro
                325                 330                 335
Thr Asn Leu Ala Gln Val Lys Gln Val Gln Gly Lys Glu Glu Thr
            340                 345                 350
Pro Ala Ser Phe Leu Glu Arg Leu Lys Glu Ala Tyr Arg Met Tyr Thr
        355                 360                 365
Pro Tyr Asp Pro Glu Asp Pro Gly Gln Ala Ala Ser Val Ile Leu Ser
    370                 375                 380
Phe Ile Tyr Gln Ser Ser Pro Asp Ile Arg Asn Lys Leu Gln Arg Leu
385                 390                 395                 400
Glu Gly Leu Gln Gly Phe Thr Leu Ser Asp Leu Leu Lys Glu Ala Glu
                405                 410                 415
Lys Ile Tyr Asn Lys Arg Glu Thr Pro Glu Glu Arg Glu Glu Arg Leu
            420                 425                 430
Trp Gln Arg Gln Glu Glu Arg Asp Lys Lys Arg His Lys Glu Met Thr
        435                 440                 445
Lys Val Leu Ala Thr Val Val Ala Gln Asn Arg Asp Lys Asp Arg Gly
    450                 455                 460
Glu Ser Lys Leu Gly Asp Gln Arg Lys Ile Pro Leu Gly Lys Asp Gln
465                 470                 475                 480
Cys Ala Tyr Cys Lys Glu Lys Gly His Trp Val Arg Asp Cys Pro Lys
                485                 490                 495
Arg Pro Arg Lys Lys Pro Ala Asn Ser Thr Leu Leu
            500                 505

<210> SEQ ID NO 5
<211> LENGTH: 1530
<212> TYPE: DNA
<213> ORGANISM: Feline leukemia virus
<220> FEATURE:
<221> NAME/KEY: misc_feature
<222> LOCATION: (1)..(1530)
<223> OTHER INFORMATION: DNA sequence of the mutagenized "gag" gene

<400> SEQUENCE: 5
atgggccaga ccatcaccac ccccctgagc ctgaccctga accactggag cgaggtgcag       60
gccagggcca ggaaccaggg cgtggaggtg aggaagaaga gtggatcac cctgtgcgag      120 gccgagtggg tgatgatgaa cgtgggctgg cccaggagg gcaccttcac catcgacaac      180
atcagccagg tggaggagag gatcttcgcc cccggcccct acggccaccc cgaccagatc      240
ccctacatca ccacctggag gagcctggcc accgaccccc cccctgggt gaggccttc       300 ctgccccccc ccaagcaccc caggaccgac ccccccgagc cctgagccc cagcccctg       360 gccccccagc cagcgccccc cccatcagc agcctgtacc ccgtgctgcc caagcccgac      420 cccccaagg ccccccgtgct gccccccaac cccagcagcc ccctgatcga cctgctgacc      480
```

```
gaggagcccc cccctaccc cggcggccac ggccccaccc ccccagcgg ccccaggacc    540 cccaccgcca gccccatcgc cagcaggctg agggagagga gggagaaccc cgccgagaag    600
agccaggccc tgcccctgag ggaggacccc aacaacaggc cccagtactg gcccttcagc    660
gccagcgacc tgtacaactg gaagctgcac aaccccccct tcagccagga ccccgtggcc    720
ctgaccaacc tgatcgagag catcctggtg acccaccagc ccacctggga cgactgccag    780
cagctgctgc aggccctgct gaccgccgag gagaggcaga gggtgctgct ggaggccagg    840
aagcaggtgc ccggcgagga cggcaggccc acccagctgc ccaacgtggt ggacgaggcc    900 ttcccccctga ccaggcccaa ctgggacttc tgcaccccccg ccggcaggga gcacctgagg    960
ctgtacaggc agctgctgct ggccggcctg aggggcgccg ccaggaggcc caccaacctg   1020
gcccaggtga agcaggtggt gcagggcaag gaggagacac ccgccagctt cctggagagg   1080
ctgaaggagg cctacaggat gtacacccccc tacgaccccg aggacccccgg ccaggccacc   1140 agcgtgatcc tgagcttcat ctaccagagc agccccgaca tcaggaacaa gctgcagagg   1200
ctggagggcc tgcagggctt caccctgagc gacctgctga aggaggccga gaagatctac   1260
aacaagaggg agacacccga ggagagggag gagaggctgt ggcagaggca ggaggagagg   1320
gacaagaaga ggcacaagga gatgaccaag gtgctggcca ccgtggtggc ccagaacagg   1380
gacaaggaca ggggcgagag caagctgggc gaccagagga gatcccccct gggcaaggac   1440
cagtgcgcct actgcaagga agggggccac tgggtgaggg actgccccaa gaggcccagg   1500
aagaagcccg ccaacagcac cctgctgtag                                   1530
```

<210> SEQ ID NO 6  
<211> LENGTH: 509  
<212> TYPE: PRT  
<213> ORGANISM: Feline leukemia virus  
<220> FEATURE:  
<221> NAME/KEY: PEPTIDE  
<222> LOCATION: (1)..(509)  
<223> OTHER INFORMATION: Amino acid sequence of the protein corresponding to Seq.ID5

<400> SEQUENCE: 6

Met Gly Gln Thr Ile Thr Thr Pro Leu Ser Leu Thr Leu Asn His Trp  
1               5                   10                  15

Ser Glu Val Gln Ala Arg Ala Arg Asn Gln Gly Val Glu Val Arg Lys  
            20                  25                  30

Lys Lys Trp Ile Thr Leu Cys Glu Ala Glu Trp Val Met Met Asn Val  
        35                  40                  45

Gly Trp Pro Arg Glu Gly Thr Phe Thr Ile Asp Asn Ile Ser Gln Val  
    50                  55                  60

Glu Glu Arg Ile Phe Ala Pro Gly Pro Tyr Gly His Pro Asp Gln Ile  
65                  70                  75                  80

Pro Tyr Ile Thr Thr Trp Arg Ser Leu Ala Thr Asp Pro Pro Trp  
                85                  90                  95

Val Arg Pro Phe Leu Pro Pro Lys His Pro Arg Thr Asp Pro Pro  
            100                 105                 110

Glu Pro Leu Ser Pro Gln Pro Leu Ala Pro Gln Pro Ser Ala Pro Pro  
        115                 120                 125

Ile Ser Ser Leu Tyr Pro Val Leu Pro Lys Pro Asp Pro Pro Lys Ala  
    130                 135                 140

Pro Val Leu Pro Pro Asn Pro Ser Ser Pro Leu Ile Asp Leu Leu Thr  
145                 150                 155                 160

| | | | | | | | | | | | |
|---|---|---|---|---|---|---|---|---|---|---|---|
|Glu|Glu|Pro|Pro|Pro|Tyr|Pro|Gly|Gly|His|Gly|Pro|Thr|Pro|Pro|Ser|
| | | |165| | | |170| | | |175|

Glu Glu Pro Pro Pro Tyr Pro Gly Gly His Gly Pro Thr Pro Pro Ser
            165                 170                 175

Gly Pro Arg Thr Pro Thr Ala Ser Pro Ile Ala Ser Arg Leu Arg Glu
            180                 185                 190

Arg Arg Glu Asn Pro Ala Glu Lys Ser Gln Ala Leu Pro Leu Arg Glu
            195                 200                 205

Asp Pro Asn Asn Arg Pro Gln Tyr Trp Pro Phe Ser Ala Ser Asp Leu
        210                 215                 220

Tyr Asn Trp Lys Leu His Asn Pro Pro Phe Ser Gln Asp Pro Val Ala
225                 230                 235                 240

Leu Thr Asn Leu Ile Glu Ser Ile Leu Val Thr His Gln Pro Thr Trp
            245                 250                 255

Asp Asp Cys Gln Gln Leu Leu Gln Ala Leu Leu Thr Ala Glu Glu Arg
            260                 265                 270

Gln Arg Val Leu Leu Glu Ala Arg Lys Gln Val Pro Gly Glu Asp Gly
            275                 280                 285

Arg Pro Thr Gln Leu Pro Asn Val Val Asp Glu Ala Phe Pro Leu Thr
            290                 295                 300

Arg Pro Asn Trp Asp Phe Cys Thr Pro Ala Gly Arg Glu His Leu Arg
305                 310                 315                 320

Leu Tyr Arg Gln Leu Leu Leu Ala Gly Leu Arg Gly Ala Ala Arg Arg
            325                 330                 335

Pro Thr Asn Leu Ala Gln Val Lys Gln Val Val Gln Gly Lys Glu Glu
            340                 345                 350

Thr Pro Ala Ser Phe Leu Glu Arg Leu Lys Glu Ala Tyr Arg Met Tyr
            355                 360                 365

Thr Pro Tyr Asp Pro Glu Asp Pro Gly Gln Ala Thr Ser Val Ile Leu
            370                 375                 380

Ser Phe Ile Tyr Gln Ser Ser Pro Asp Ile Arg Asn Lys Leu Gln Arg
385                 390                 395                 400

Leu Glu Gly Leu Gln Gly Phe Thr Leu Ser Asp Leu Leu Lys Glu Ala
            405                 410                 415

Glu Lys Ile Tyr Asn Lys Arg Glu Thr Pro Glu Glu Arg Glu Glu Arg
            420                 425                 430

Leu Trp Gln Arg Gln Glu Glu Arg Asp Lys Lys Arg His Lys Glu Met
            435                 440                 445

Thr Lys Val Leu Ala Thr Val Val Ala Gln Asn Arg Asp Lys Asp Arg
            450                 455                 460

Gly Glu Ser Lys Leu Gly Asp Gln Arg Lys Ile Pro Leu Gly Lys Asp
465                 470                 475                 480

Gln Cys Ala Tyr Cys Lys Glu Lys Gly His Trp Val Arg Asp Cys Pro
            485                 490                 495

Lys Arg Pro Arg Lys Lys Pro Ala Asn Ser Thr Leu Leu
            500                 505

<210> SEQ ID NO 7
<211> LENGTH: 1929
<212> TYPE: DNA
<213> ORGANISM: Feline leukemia virus
<220> FEATURE:
<221> NAME/KEY: misc_feature
<222> LOCATION: (1)..(1929)
<223> OTHER INFORMATION: DNA sequence for the mutagenized "env" gene
      (gp85)

<400> SEQUENCE: 7
atggagtccc ccaccccaccc caagccctcc aaggacaaga ccctgtcctg gaacatggtg    60

```
ttcctggtgg gcatcctgtt caccattgac attggcatgg ccaacccctc cccccccgg      120 atctacaatg tgacctgggt gatcaccaat gtgcagacca cacccaggc caatgccacc      180 tctatgctgg gcaccctgac agatgcatac cccaccctgc atgtggacct gtgtgacctg     240
gtgggggaca cctgggagcc cattccgctg aaccccacca atgtgaagca tggggccagg     300
tactcctcct ccaagtatgg ctgcaagacc acagacagga agaagcagca gcagacctac     360
cccttctatg tgtgccctgg ccatgccccc tccctgggcc caagggcac ccactgtggg      420 ggggcccagg atggcttctg tgctgcctgg ggctgtgaaa ccacagggga ggcctggtgg     480
aagcccacct cctcctggga ctacatcaca gtgaagaggg gctcctccca ggacaactcc     540
tgtgagggca gtgcaaccc cctggtgctg cagttcaccc agaagggcag gcaggcctcc      600
tgggatggcc ccaagatgtg gggcctgagg ctgtacagga caggctatga ccccattgcc     660
ctgttcacag tgtccaggca ggtgtccacc atcacccccc ccaggccat gggccccaac      720 ctggtgctgc ctgaccagaa gcccccctcc aggcagtccc agacaggctc caaggtggcc    780
acccagaggc ccagaccaa tgagtctgcc cccaggtctg tggccccac caccatgggc      840 cccaagagga ttggcacagg ggacaggctg atcaacctgg tgcagggcac ctacctggcc    900
ctgaatgcca cagaccccaa caagaccaag gactgctggc tgtgcctggt gtccaggccc    960
ccctactatg agggcattgc catcctgggc aactactcca accagaccaa ccccccccc     1020 tcctgcctgt ccacccccca gcacaagctg accatctctg aggtgtctgg ccagggcatg   1080
tgcattggca cagtgcccaa gacccaccag gccctgtgca acaagaccca gcagggccac    1140
acaggggccc actacctggc tgtccccaat ggcacctact gggcctgcaa cacaggcctg    1200 acccctgca tctccatggc tgtgctgaac tggacctctg acttctgtgt gctgattgag      1260
ctgtggccca gggtgaccta ccaccagcct gagtatgtgt acacccactt tgccaaggct    1320
gtgaggttca ggagggagcc catctccctg acagtggccc tgatgctggg gggcctgaca    1380 gtgggggca ttgctgctgg ggtgggcaca ggcaccaagg ccctgctgga aacagcccag     1440
ttcagacaac tacaaatggc catgcacaca gacatccagg ccctagaaga gtcagttagc    1500
gctttagaaa atccctgac ctccctctct gaagtagtcc tacaaaacag acgaggccta     1560
gatattctat tcctacaaga gggaggactc tgtgccgcat aaaagaaga atgttgtttt    1620 tatgcagatc acaccggatt agtccgagat aatatggcta aattaagaga aagattaaaa   1680
cagcggcaac aactgtttga ctcccaacag ggatggtttg aaggatggtt caacaagtcc    1740
ccctggctta caaccctaat ttcctctatt atgggcccct tgcttatcct gctcctaatt   1800
ctcctcttcg gccatgcat ccttaaccga ttggtgcaat tcgtaaaaga cagaatatcg    1860
gtggtacaag ccttagtttt aaccccaacag taccaacaga taaagcaata cgatccggac   1920
cgaccatga                                                           1929
```

<210> SEQ ID NO 8
<211> LENGTH: 1440
<212> TYPE: DNA
<213> ORGANISM: Feline leukemia virus
<220> FEATURE:
<221> NAME/KEY: misc_feature
<222> LOCATION: (1)..(1440)
<223> OTHER INFORMATION: DNA Sequence of the mutagenized "env" gene (gp70)

<400> SEQUENCE: 8

```
atggagtccc ccacccaccc caagccctcc aaggacaaga ccctgtcctg gaacatggtg      60
```

-continued

```
ttcctggtgg gcatcctgtt caccattgac attggcatgg ccaaccccta ccccccccgg      120
atctacaatg tgacctgggt gatcaccaat gtgcagacca cacccaggc caatgccacc       180 tctatgctgg gcaccctgac agatgcatac cccaccctgc atgtggacct gtgtgacctg      240
gtgggggaca cctgggagcc cattccgctg aaccccacca atgtgaagca tggggccagg      300
tactcctcct ccaagtatgg ctgcaagacc acagacagga agaagcagca gcagacctac      360
cccttctatg tgtgccctgg ccatgccccc tccctgggcc caagggcac ccactgtggg       420 ggggcccagg atggcttctg tgctgcctgg ggctgtgaaa ccacagggga ggcctggtgg      480
aagcccacct cctcctggga ctacatcaca gtgaagaggg gctcctccca ggacaactcc     540
tgtgagggca agtgcaaccc cctggtgctg cagttcaccc agaagggcag gcaggcctcc     600
tgggatggcc ccaagatgtg gggcctgagg ctgtacagga caggctatga ccccattgcc     660
ctgttcacag tgtccaggca ggtgtccacc atcaccccc cccaggccat gggccccaac      720
ctggtgctgc ctgaccagaa gcccccctcc aggcagtccc agacaggctc caaggtggcc     780
acccagaggc cccagaccaa tgagtctgcc cccaggtctg tggcccccac caccatgggc    840
cccaagagga ttggcacagg ggacaggctg atcaacctgg tgcagggcac ctacctggcc    900
ctgaatgcca cagaccccaa caagaccaag gactgctggc tgtgcctggt gtccaggccc    960
ccctactatg agggcattgc catcctgggc aactactcca accagaccaa ccccccccc    1020 tcctgcctgt ccaccccca gcacaagctg accatctctg aggtgtctgg ccagggcatg    1080
tgcattggca cagtgcccaa gacccaccag gccctgtgca acaagaccca gcagggccac   1140
acaggggccc actacctggc tgtccccaat ggcacctact gggcctgcaa cacaggcctg    1200 acccctgca tctccatggc tgtgctgaac tggacctctg acttctgtgt gctgattgag     1260
ctgtggccca gggtgaccta ccaccagcct gagtatgtgt acacccactt tgccaaggct    1320
gtgaggttca ggagggagcc catctccctg acagtggccc tgatgctggg gggcctgaca    1380 gtgggggca ttgctgctgg ggtgggcaca ggcaccaagg ccctgctgga aacagcctga    1440
```

<210> SEQ ID NO 9
<211> LENGTH: 642
<212> TYPE: PRT
<213> ORGANISM: Feline leukemia virus
<220> FEATURE:
<221> NAME/KEY: PEPTIDE
<222> LOCATION: (1)..(642)
<223> OTHER INFORMATION: Amino acid sequence of the protein
      corresponding to Seq.ID7

<400> SEQUENCE: 9

```
Met Glu Ser Pro Thr His Pro Lys Pro Ser Lys Asp Lys Thr Leu Ser
1               5                   10                  15

Trp Asn Met Val Phe Leu Val Gly Ile Leu Phe Thr Ile Asp Ile Gly
                20                  25                  30

Met Ala Asn Pro Ser Pro Arg Ile Tyr Asn Val Thr Trp Val Ile
            35                  40                  45

Thr Asn Val Gln Thr Asn Thr Gln Ala Asn Ala Thr Ser Met Leu Gly
        50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Pro Leu Asn Pro Thr Asn Val Lys
                85                  90                  95

His Gly Ala Arg Tyr Ser Ser Ser Lys Tyr Gly Cys Lys Thr Thr Asp
                100                 105                 110
```

-continued

```
Arg Lys Lys Gln Gln Gln Thr Tyr Pro Phe Tyr Val Cys Pro Gly His
    115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
    195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
    275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
    355                 360                 365

His Gln Ala Leu Cys Asn Lys Thr Gln Gln Gly His Thr Gly Ala His
    370                 375                 380

Tyr Leu Ala Val Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
    435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Val Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
    515                 520                 525

Gly Leu Cys Ala Ala Leu Lys Glu Glu Cys Cys Phe Tyr Ala Asp His
    530                 535                 540
```

```
Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Leu Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Val Leu Thr Gln Gln Tyr Gln Gln Ile Lys Gln Tyr Asp Pro Asp
625                 630                 635                 640

Arg Pro

<210> SEQ ID NO 10
<211> LENGTH: 479
<212> TYPE: PRT
<213> ORGANISM: Feline leukemia virus
<220> FEATURE:
<221> NAME/KEY: PEPTIDE
<222> LOCATION: (1)..(479)
<223> OTHER INFORMATION: Amino acid sequence of the protein
      corresponding to Seq.ID8

<400> SEQUENCE: 10

Met Glu Ser Pro Thr His Pro Lys Pro Ser Lys Asp Lys Thr Leu Ser
1               5                   10                  15

Trp Asn Met Val Phe Leu Val Gly Ile Leu Phe Thr Ile Asp Ile Gly
                20                  25                  30

Met Ala Asn Pro Ser Pro Arg Ile Tyr Asn Val Thr Trp Val Ile
            35                  40                  45

Thr Asn Val Gln Thr Asn Thr Gln Ala Asn Ala Thr Ser Met Leu Gly
        50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Pro Leu Asn Pro Thr Asn Val Lys
                85                  90                  95

His Gly Ala Arg Tyr Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
```

```
                            245                  250                  255
Ser Lys Val Ala Thr Gln Arg Pro Gln Thr Asn Glu Ser Ala Pro Arg
        260                  265                  270

Ser Val Ala Pro Thr Thr Met Gly Pro Lys Arg Ile Gly Thr Gly Asp
        275                  280                  285

Arg Leu Ile Asn Leu Val Gln Gly Thr Tyr Leu Ala Leu Asn Ala Thr
        290                  295                  300

Asp Pro Asn Lys Thr Lys Asp Cys Trp Leu Cys Leu Val Ser Arg Pro
305                  310                  315                  320

Pro Tyr Tyr Glu Gly Ile Ala Ile Leu Gly Asn Tyr Ser Asn Gln Thr
                325                  330                  335

Asn Pro Pro Pro Ser Cys Leu Ser Thr Pro Gln His Lys Leu Thr Ile
                340                  345                  350

Ser Glu Val Ser Gly Gln Gly Met Cys Ile Gly Thr Val Pro Lys Thr
                355                  360                  365

His Gln Ala Leu Cys Asn Lys Thr Gln Gln Gly His Thr Gly Ala His
        370                  375                  380

Tyr Leu Ala Val Pro Asn Gly Thr Tyr Trp Ala Cys Asn Thr Gly Leu
385                  390                  395                  400

Thr Pro Cys Ile Ser Met Ala Val Leu Asn Trp Thr Ser Asp Phe Cys
                405                  410                  415

Val Leu Ile Glu Leu Trp Pro Arg Val Thr Tyr His Gln Pro Glu Tyr
                420                  425                  430

Val Tyr Thr His Phe Ala Lys Ala Val Arg Phe Arg Arg Glu Pro Ile
                435                  440                  445

Ser Leu Thr Val Ala Leu Met Leu Gly Gly Leu Thr Val Gly Gly Ile
        450                  455                  460

Ala Ala Gly Val Gly Thr Gly Thr Lys Ala Leu Leu Glu Thr Ala
465                  470                  475
```

<210> SEQ ID NO 11
<211> LENGTH: 1440
<212> TYPE: DNA
<213> ORGANISM: Feline leukemia virus
<220> FEATURE:
<221> NAME/KEY: gene
<222> LOCATION: (1)..(1440)
<223> OTHER INFORMATION: DNA sequence of wildtype "env" gene (gp70)

<400> SEQUENCE: 11

```
atggaaagtc caacgcaccc aaaaccctct aaagataaga ctctctcgtg gaacttagcg    60
tttctggtgg ggatcttatt tacaatagac ataggaatgg ccaatcctag tccacaccaa   120
atatataatg taacttgggt aataaccaat gtacaaacta cacccaagc taacgccacc   180 tctatgttag gaaccttaac cgatgcctac cctaccctac atgttgactt atgtgaccta   240
gtgggagaca cctgggaacc tatagtccta aacccaacca atgtaaaaca cggggcacgt   300
tactcctcct caaaatatgg atgtaaaact acagatagaa aaaacagca acagacatac   360 ccctttacg tctgccccgg acatgccccc tcgttgggc caagggaac acattgtgga   420 ggggcacaag atgggttttg tgccgcatgg ggatgtgaga ccaccggaga agcttggtgg   480
aagcccacct cctcatggga ctatatcaca gtaaaaagag ggagtagtca ggacaatagc   540
tgtgagggaa aatgcaaccc cctggttttg cagttcaccc agaagggaag acaagcctct   600
tgggacggac ctaagatgtg ggattgcga ctataccgta caggtatga ccctatcgct   660 ttattcacgg tgtcccggca ggtatcaacc attacgccgc ctcaggcaat gggaccaaac   720
```

```
ctagtcttac ctgatcaaaa accccatcc cgacaatctc aaacagggtc caaagtggcg      780
acccagaggc cccaaacgaa tgaaagcgcc ccaaggtctg ttgccccac caccatgggt      840 cccaaacgga ttgggaccgg agataggtta ataaatttag tacaagggac atacctagcc     900
ttaaatgcca ccgaccccaa caaaactaaa gactgttggc tctgcctggt ttctcgacca     960
ccctattacg aagggattgc aatcttaggt aactacagca accaaacaaa ccccccccca   1020
tcctgcctat ctactccgca acacaaacta actatatctg aagtatcagg caaggaatg    1080 tgcataggga ctgttcctaa aacccaccag gctttgtgca ataagacaca acagggacat   1140
acaggggcgc actatctagc cgcccccaac ggcacctatt gggcctgtaa cactggactc   1200
accccatgca tttccatggc ggtgctcaat tggacctctg attttgtgt cttaatcgaa    1260 ttatggccca gagtgactta ccatcaaccc gaatatgtgt acacacattt tgccaaagct   1320
gtcaggttcc gaagagaacc aatatcacta acggttgccc ttatgttggg aggacttact   1380
gtagggggca tagccgcggg ggtcggaaca gggactaaag ccctccttga aacagcctga   1440
```

<210> SEQ ID NO 12
<211> LENGTH: 42
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(42)
<223> OTHER INFORMATION: gag-mut1-rneu

<400> SEQUENCE: 12
aattaagagc tccacgtctc ccccgctaa cagcaactgg cg                          42

<210> SEQ ID NO 13
<211> LENGTH: 45
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(45)
<223> OTHER INFORMATION: gag-mut2-l

<400> SEQUENCE: 13
aattaagagc tccaggtctc cggggctccg cggggctgca agacg                      45

<210> SEQ ID NO 14
<211> LENGTH: 48
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(48)
<223> OTHER INFORMATION: gag-mut3-r

<400> SEQUENCE: 14
aattaagagc tccacgtctc cttcccttt gttgtatatc ttttctgc                    48

<210> SEQ ID NO 15
<211> LENGTH: 48
<212> TYPE: DNA
<213> ORGANISM: Artificial Sequence
<220> FEATURE:
<223> OTHER INFORMATION: synthetic DNA primer
<220> FEATURE:

```
<221> NAME/KEY: misc_feature
<222> LOCATION: (1)..(48)
<223> OTHER INFORMATION: gag-mut4-l

<400> SEQUENCE: 15
aattaagagc tccaggtctc cggaaacccc agaggaaagg gaagaaag                    48

<210> SEQ ID NO 16
<211> LENGTH: 34
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(34)
<223> OTHER INFORMATION: Felvgag-l

<400> SEQUENCE: 16
cggataaggt accatgggcc aaactataac tacc                                  34

<210> SEQ ID NO 17
<211> LENGTH: 37
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(37)
<223> OTHER INFORMATION: Felvgag-r

<400> SEQUENCE: 17
ttctcagagc tcttagagga gagtggagtt ggcgggt                               37

<210> SEQ ID NO 18
<211> LENGTH: 33
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(33)
<223> OTHER INFORMATION: envl

<400> SEQUENCE: 18
cggataaggt accatggcca atcctagtcc acc                                   33

<210> SEQ ID NO 19
<211> LENGTH: 37
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(37)
<223> OTHER INFORMATION: envr

<400> SEQUENCE: 19
agttctcaga gctcttaggc tgtttcaagg agggctt                               37

<210> SEQ ID NO 20
<211> LENGTH: 28
<212> TYPE: DNA
<213> ORGANISM: Artificial Sequence
<220> FEATURE:
<223> OTHER INFORMATION: synthetic DNA primer
<220> FEATURE:
```

<221> NAME/KEY: misc_feature
<222> LOCATION: (1)..(28)
<223> OTHER INFORMATION: Primer

<400> SEQUENCE: 20
atattggatc ccatggccaa cccctccc                                              28

<210> SEQ ID NO 21
<211> LENGTH: 34
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(34)
<223> OTHER INFORMATION: Primer

<400> SEQUENCE: 21
attatggtct cctgctgctt cttcctgtct gtgg                                       34

<210> SEQ ID NO 22
<211> LENGTH: 30
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(30)
<223> OTHER INFORMATION: Primer

<400> SEQUENCE: 22
taataggtct ccagcagcag acctacccct                                            30

<210> SEQ ID NO 23
<211> LENGTH: 33
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(33)
<223> OTHER INFORMATION: Primer

<400> SEQUENCE: 23
taataggtct ctgtgaacag ggcaatgggg tca                                        33

<210> SEQ ID NO 24
<211> LENGTH: 34
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(34)
<223> OTHER INFORMATION: Primer

<400> SEQUENCE: 24
tatttggtct cttcacagtg tccaggcagg tgtc                                       34

<210> SEQ ID NO 25
<211> LENGTH: 30
<212> TYPE: DNA
<213> ORGANISM: Artificial Sequence
<220> FEATURE:
<223> OTHER INFORMATION: synthetic DNA primer
<220> FEATURE:

```
<221> NAME/KEY: misc_feature
<222> LOCATION: (1)..(30)
<223> OTHER INFORMATION: Primer

<400> SEQUENCE: 25
tattaggtct cagcttgtgc tgggggggtgg                                          30

<210> SEQ ID NO 26
<211> LENGTH: 34
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(34)
<223> OTHER INFORMATION: Primer

<400> SEQUENCE: 26
aataaggtct ccaagctgac catctctgag gtgt                                      34

<210> SEQ ID NO 27
<211> LENGTH: 27
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(27)
<223> OTHER INFORMATION: Primer

<400> SEQUENCE: 27
attaagagct ctcaggctgt ttccagc                                              27

<210> SEQ ID NO 28
<211> LENGTH: 31
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(31)
<223> OTHER INFORMATION: Primer

<400> SEQUENCE: 28
attgccggta ccatggagtc ccccacccac c                                         31

<210> SEQ ID NO 29
<211> LENGTH: 35
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(35)
<223> OTHER INFORMATION: Primer

<400> SEQUENCE: 29
atcagaggtc tcccatgcca atgtcaatgg tgaac                                     35

<210> SEQ ID NO 30
<211> LENGTH: 27
<212> TYPE: DNA
<213> ORGANISM: Artificial Sequence
<220> FEATURE:
<223> OTHER INFORMATION: synthetic DNA primer
<220> FEATURE:
```

<221> NAME/KEY: misc_feature
<222> LOCATION: (1)..(27)
<223> OTHER INFORMATION: Primer

<400> SEQUENCE: 30
gatctgggtc tccatggcca acccctc                                          27

<210> SEQ ID NO 31
<211> LENGTH: 36
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(36)
<223> OTHER INFORMATION: Primer

<400> SEQUENCE: 31
aattatggtc tcgcagttca gacaactaca aatggc                                36

<210> SEQ ID NO 32
<211> LENGTH: 30
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(30)
<223> OTHER INFORMATION: Primer

<400> SEQUENCE: 32
aattatgagc tctcagggcc tgtcagggtc                                       30

<210> SEQ ID NO 33
<211> LENGTH: 28
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(28)
<223> OTHER INFORMATION: Primer

<400> SEQUENCE: 33
aattatggta ccatggagtc ccccaccc                                         28

<210> SEQ ID NO 34
<211> LENGTH: 35
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(35)
<223> OTHER INFORMATION: Primer

<400> SEQUENCE: 34
tataatggtc tcaactgggc tgtttccagc agggc                                 35

<210> SEQ ID NO 35
<211> LENGTH: 31
<212> TYPE: DNA
<213> ORGANISM: Artificial Sequence
<220> FEATURE:
<223> OTHER INFORMATION: synthetic DNA primer
<220> FEATURE:

```
<221> NAME/KEY: misc_feature
<222> LOCATION: (1)..(31)
<223> OTHER INFORMATION: Primer

<400> SEQUENCE: 35
atattaggtc tcagatccgg ggggggagg g                              31

<210> SEQ ID NO 36
<211> LENGTH: 30
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(30)
<223> OTHER INFORMATION: Primer

<400> SEQUENCE: 36
atattggtct caggagaggg acaagaagag                               30

<210> SEQ ID NO 37
<211> LENGTH: 32
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(32)
<223> OTHER INFORMATION: Primer

<400> SEQUENCE: 37
aatatggtct ctcagcctgc tggcgatggg gc                            32

<210> SEQ ID NO 38
<211> LENGTH: 32
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(32)
<223> OTHER INFORMATION: Primer

<400> SEQUENCE: 38
attatggtct ctgcacctga ggctgtacag gc                            32

<210> SEQ ID NO 39
<211> LENGTH: 36
<212> TYPE: DNA
<213> ORGANISM: Artificial Sequence
<220> FEATURE:
<223> OTHER INFORMATION: synthetic DNA primer
<220> FEATURE:
<221> NAME/KEY: misc_feature
<222> LOCATION: (1)..(36)
<223> OTHER INFORMATION: Primer

<400> SEQUENCE: 39
aatatggtct cggtgctccc tgccggcggg ggtgca                        36

<210> SEQ ID NO 40
<211> LENGTH: 28
<212> TYPE: DNA
<213> ORGANISM: Artificial Sequence
<220> FEATURE:
<223> OTHER INFORMATION: synthetic DNA primer
<220> FEATURE:
```

-continued

```
<221> NAME/KEY: misc_feature
<222> LOCATION: (1)..(28)
<223> OTHER INFORMATION: Primer

<400> SEQUENCE: 40
aatatggtct ctctcctcct gcctctgc                                          28

<210> SEQ ID NO 41
<211> LENGTH: 7
<212> TYPE: PRT
<213> ORGANISM: Simian virus 40

<400> SEQUENCE: 41

Pro Lys Lys Lys Arg Lys Val
1               5
```